(12) United States Patent
Hansen

(10) Patent No.: US 8,057,486 B2
(45) Date of Patent: Nov. 15, 2011

(54) APPARATUS AND METHOD FOR INSERTING IMPLANTS INTO THE BODY

(75) Inventor: Morten Hansen, Valencia, CA (US)

(73) Assignee: Bioness Inc., Valencia, CA (US)

( * ) Notice: Subject to any disclaimer, the term of this patent is extended or adjusted under 35 U.S.C. 154(b) by 1092 days.

(21) Appl. No.: 11/856,833

(22) Filed: Sep. 18, 2007

(65) Prior Publication Data

US 2009/0076521 A1  Mar. 19, 2009

(51) Int. Cl.
*A61N 1/05* (2006.01)

(52) U.S. Cl. .......................... 606/129; 607/116

(58) Field of Classification Search .............. 606/129; 607/115

See application file for complete search history.

(56) References Cited

U.S. PATENT DOCUMENTS

| | | |
|---|---|---|
| 3,204,637 A | 9/1965 | Frank et al. |
| 3,426,748 A | 2/1969 | Bowers |
| 4,166,469 A | 9/1979 | Littleford |
| 4,306,560 A | 12/1981 | Harris |
| 4,898,183 A | 2/1990 | Kuzma |
| 4,958,901 A * | 9/1990 | Coombs .......................... 604/44 |
| 5,003,990 A | 4/1991 | Osypka |
| 5,170,787 A | 12/1992 | Lindegren |
| 5,300,106 A | 4/1994 | Dahl et al. |
| 5,304,218 A | 4/1994 | Alferness |
| 5,439,464 A | 8/1995 | Shapiro |
| 5,443,493 A | 8/1995 | Byers et al. |
| 5,586,553 A * | 12/1996 | Halili et al. .................... 600/316 |
| 5,667,514 A | 9/1997 | Heller |
| 5,782,841 A | 7/1998 | Ritz et al. |
| 5,797,923 A | 8/1998 | Aiyar et al. |
| 5,984,890 A | 11/1999 | Gast et al. |
| 6,051,017 A | 4/2000 | Loeb et al. |
| 6,119,044 A | 9/2000 | Kuzma |
| 6,132,456 A | 10/2000 | Sommer et al. |
| 6,149,657 A | 11/2000 | Kuzma |
| 6,185,464 B1 | 2/2001 | Bonner et al. |
| 6,214,032 B1 | 4/2001 | Loeb et al. |
| 6,304,785 B1 | 10/2001 | McCreery et al. |
| 6,304,787 B1 | 10/2001 | Kuzma et al. |
| 6,332,089 B1 | 12/2001 | Acker et al. |

(Continued)

OTHER PUBLICATIONS

Salter et al., "First Clinical Experience with BION Implants for Therapeutic Electrical Stimulation," A.E. Mann Institute for Biomedical Engineering, © 1994 International Neuromodulation Society; 1094-7159, Neuromodulation, vol. 7, No. 1, 2004 38-47.

(Continued)

*Primary Examiner* — Eric D. Bertram
(74) *Attorney, Agent, or Firm* — Cooley LLP

(57) ABSTRACT

An apparatus includes a first tubular member and a second tubular member coupled to the first tubular member. The first tubular member defines a longitudinal axis and a lumen substantially coaxial with the longitudinal axis. The lumen of the first tubular member is configured to receive at least a portion of an elongate implant. A distal end portion of the first tubular member is tapered along the longitudinal axis. The second tubular member defines a longitudinal axis and a lumen substantially coaxial with the longitudinal axis of the second tubular member. The second tubular member is coupled to the first tubular member such that the longitudinal axis of the first tubular member is substantially parallel to the longitudinal axis of the second tubular member. A distal end portion of the second tubular member is tapered along the longitudinal axis of the second tubular member.

46 Claims, 10 Drawing Sheets

U.S. PATENT DOCUMENTS

| | | |
|---|---|---|
| 6,360,750 B1 | 3/2002 | Gerber et al. |
| 6,379,346 B1 | 4/2002 | McIvor et al. |
| 6,505,075 B1 | 1/2003 | Weiner |
| 6,553,264 B2 | 4/2003 | Redko et al. |
| 6,582,441 B1 | 6/2003 | He et al. |
| 6,605,094 B1 | 8/2003 | Mann et al. |
| 6,697,677 B2 | 2/2004 | Dahl et al. |
| 6,829,508 B2 | 12/2004 | Schulman et al. |
| 6,968,238 B1 | 11/2005 | Kuzma |
| 6,999,819 B2 | 2/2006 | Swoyer et al. |
| 7,018,384 B2 | 3/2006 | Skakoon |
| 7,050,858 B1 | 5/2006 | Kuzma et al. |
| 7,063,708 B2 | 6/2006 | Gibson et al. |
| 7,092,765 B2 | 8/2006 | Geske et al. |
| 7,151,965 B2 | 12/2006 | Osypka |
| 7,200,444 B2 | 4/2007 | Gavronsky et al. |
| 7,513,257 B2 | 4/2009 | Schulman et al. |
| 7,526,342 B2 * | 4/2009 | Chin et al. .................... 607/119 |
| 2003/0078618 A1 | 4/2003 | Fey et al. |
| 2004/0116878 A1 | 6/2004 | Byrd et al. |
| 2005/0113894 A1 | 5/2005 | Zilberman et al. |
| 2005/0251237 A1 | 11/2005 | Kuzma et al. |
| 2007/0078503 A1 | 4/2007 | Kuzma et al. |
| 2007/0156012 A1 | 7/2007 | Tracey et al. |
| 2007/0249992 A1 | 10/2007 | Bardy |
| 2008/0269740 A1 | 10/2008 | Bonde et al. |
| 2009/0105743 A1 | 4/2009 | Chu |
| 2009/0182401 A1 | 7/2009 | Glukhovsky |
| 2009/0182402 A1 | 7/2009 | Glukhovsky |
| 2009/0182403 A1 | 7/2009 | Glukhovsky |
| 2010/0036465 A1 | 2/2010 | Glukhovsky et al. |
| 2010/0174306 A1 | 7/2010 | Mitelberg et al. |
| 2010/0240240 A1 | 9/2010 | Ochoa et al. |

OTHER PUBLICATIONS

International Search Report and Written Opinion for PCT/US2008/070033, mailed Oct. 22, 2008, 13 pages.

* cited by examiner

APPARATUS AND METHOD FOR INSERTING IMPLANTS INTO THE BODY

BACKGROUND

The invention relates generally to medical devices and procedures, and more particularly to apparatus and methods for inserting elongate implants into the body.

Elongate implants, such as, for example, electrical stimulation leads and/or electrical sensing leads, are used in various medical procedures. For example, some known elongate implants can be implanted within a patient's body to stimulate a response from a bodily organ or tissue, such as, for example, the heart, a muscle group or the like. Some known elongate implants can be implanted within a patient's body to sense a response from a bodily organ or tissue. Accordingly, known elongate implants can be inserted into the patient's body in a known location and/or orientation (e.g., such that a portion of the elongate implant is in electrical contact with a nerve).

Known methods for inserting elongate implants within a patient's body can include first locating a desired target tissue using an electric stimulating probe and then inserting the elongate implant using a cannula. Such methods, however, often fail to detect movement of the cannula that can result in inaccuracies in the location and/or orientation of the elongate member.

Thus, a need exists for improved apparatus and methods for inserting elongate implants within a patient's body.

SUMMARY

Apparatus and methods for placing elongate implants within the body are described herein. In some embodiments, an apparatus includes a first tubular member and a second tubular member coupled to the first tubular member. The first tubular member defines a longitudinal axis and a lumen substantially coaxial with the longitudinal axis. The lumen of the first tubular member is configured to receive at least a portion of an elongate implant. A distal end portion of the first tubular member is tapered along the longitudinal axis. The second tubular member defines a longitudinal axis and a lumen substantially coaxial with the longitudinal axis of the second tubular member. The second tubular member is coupled to the first tubular member such that the longitudinal axis of the first tubular member is substantially parallel to the longitudinal axis of the second tubular member. A distal end portion of the second tubular member is tapered along the longitudinal axis of the second tubular member.

DETAILED DESCRIPTION

Figure 1:
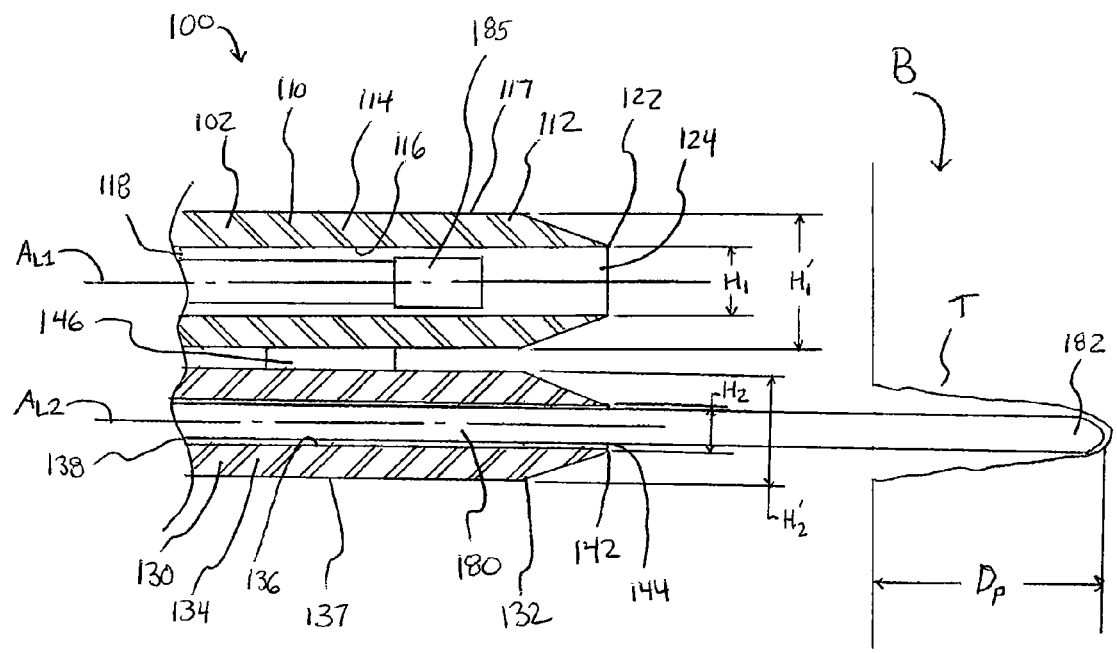
FIGS. 1 and 2 are schematic illustrations of a medical device according to an embodiment of the invention in a first configuration and a second configuration, respectively.

In some embodiments, an apparatus includes a first tubular member and a second tubular member coupled to the first tubular member. The first tubular member defines a longitudinal axis and a lumen substantially coaxial with the longitudinal axis. The lumen of the first tubular member is configured to receive at least a portion of an elongate implant. A distal end portion of the first tubular member is tapered along the longitudinal axis. The second tubular member defines a longitudinal axis and a lumen substantially coaxial with the longitudinal axis of the second tubular member. The second tubular member is coupled to the first tubular member such that the longitudinal axis of the first tubular member is substantially parallel to the longitudinal axis of the second tubular member. In some embodiments, the lumen of the second tubular member is configured to receive an electronic probe. A distal end portion of the second tubular member is tapered along the longitudinal axis of the second tubular member.

In some embodiments, an apparatus includes an implant delivery device configured to deliver an elongate implant into a body. The implant delivery device has a first portion and a second portion. The first portion defines a lumen configured to receive the elongate implant. A distal end portion of the first portion is configured to dilate a bodily tissue and defines an opening in fluid communication with the lumen. In some embodiments, for example, the distal end portion of the first portion is tapered along a longitudinal axis of the first portion. The second portion defines a lumen configured to receive a targeting probe, such as for example, an electronic probe. A distal end portion of the second portion defines an opening in fluid communication with the lumen of the second portion.

In some embodiments, an apparatus includes an implant delivery device configured to selectively position an elongate implant into a body. The implant delivery device defines a longitudinal axis and has a first portion and a second portion. The first portion defines a lumen configured to receive the elongate implant. A distal end surface of the first portion defines an opening in fluid communication with the lumen. A distal-most point of the distal end surface of the first portion is disposed at a first position along the longitudinal axis. The second portion defines a lumen configured to receive a targeting probe. A distal end surface of the second portion defines an opening in fluid communication with the lumen of the second portion. A distal-most point of the distal end surface of the second portion is disposed at a second position along the longitudinal axis, the second position spaced apart proximally from the first position. In some embodiments, the distal end surface of the first portion is configured to dilate a bodily tissue.

In some embodiments, an apparatus includes an elongate member configured to insert an electrical stimulation lead into a body, a sheath, and an actuator. The elongate member has a proximal end portion and a distal end portion. The elongate member defines a first lumen and a second lumen. The distal end portion of the elongate member is configured to dilate a bodily tissue and defines a first opening in fluid communication with the first lumen and a second opening in fluid communication with the second lumen. The sheath is slidably disposed about the elongate member. The actuator is coupled to the proximal end portion of the elongate member and is configured to move the elongate member relative to the sheath.

In some embodiments, a kit includes an implant delivery device configured to deliver an electrical stimulation lead into a body, the electrical stimulation lead, and a targeting probe. The implant delivery device includes an elongate member, a sheath, and an actuator. The elongate member has a proximal end portion and a distal end portion. The elongate member defines a first lumen and a second lumen. The distal end portion of the elongate member is configured to dilate a bodily tissue and defines a first opening in fluid communication with the first lumen and a second opening in fluid communication with the second lumen. The sheath is slidably disposed about the elongate member. The actuator is coupled to the proximal end portion of the elongate member and is configured to move the elongate member within the sheath. The electrical stimulation lead is configured to be disposed within the first lumen. The targeting probe is configured to be slidably disposed within the second lumen.

In some embodiments, a method includes inserting a targeting probe into a body, the targeting probe having a distal end portion and a central portion. An implant delivery device is inserted into the body. The implant delivery device includes an elongate member, an electrical stimulation lead, and a retention member. The elongate member defines a first lumen and a second lumen. The electrical stimulation lead is disposed within the first lumen. The retention member is configured to limit movement of the electrical stimulation lead within the first lumen. The implant delivery device is inserted after the targeting probe is inserted such that at least the central portion of the targeting probe is disposed within the second lumen and the distal end portion of the targeting probe is disposed outside of the second lumen. The elongate member of the implant delivery device is moved relative to the retention member such that a distal end portion of the electrical stimulation lead is disposed outside of the first lumen.

As used in this specification, the words "proximal" and "distal" refer to the direction closer to and away from, respectively, an operator (e.g., surgeon, physician, nurse, technician, etc.) who would use a medical device or a therapeutic device during a procedure. For example, the end of a medical device first to contact and/or be inserted into the patient's body would be the distal end, while the opposite end of the medical device (e.g., the end of the medical device being operated by the operator or the end of the medical device last to be inserted into the patient's body) would be the proximal end of the medical device.

The term "parallel" is used herein to describe a relationship between two objects (e.g., a first tubular member, a second tubular member, a lumen or the like) and/or the geometric constructions defined by two objects (e.g., a longitudinal axis) in which the two objects and/or the two geometric constructions are substantially non-intersecting if they extend substantially to infinity. For example, as used herein in the context of geometrical constructions, when a planar surface (i.e., a two-dimensional surface) is said to be parallel to a line (e.g., a longitudinal axis), every point along the line is spaced apart from the nearest portion of the planar surface by a substantially equal distance. Similarly, as used herein in the context of two objects, a first object (e.g., a first tubular member) is said to be parallel to a second object (e.g., a second tubular member) when a longitudinal axis of the first object and a longitudinal axis of the second object do not intersect if they were extended to infinity. Two objects and/or geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances or the like.

The term "normal" is used herein to describe a relationship between two objects (e.g., a first tubular member, a second tubular member, a lumen or the like) and/or the geometric constructions defined by two objects (e.g., a longitudinal axis, a planar surface or the like) in which the two objects and/or the two geometric constructions intersect at an angle of approximately 90 degrees within at least one plane. For example, as used herein in the context of two objects, a first object is said to be normal to a second object when a longitudinal axis of the first object and a longitudinal axis of the second object intersect at an angle of approximately 90 degrees within a plane.

The terms "member" and "device" as used herein can refer to either a single item or multiple items that cooperatively perform a function. For example, as used herein, a "tubular member" can include a single component or can be constructed from multiple components coupled together. More particularly, when a tubular member includes a single component, the single component can be, but is not necessarily, monolithically constructed from a single material. When a tubular member is constructed from multiple components, in some embodiments, the various components can move relative to each other. Conversely, in other embodiments, the various components from which the tubular member is constructed can be in a fixed position relative to each other whether or not monolithically formed.

Figure 2:
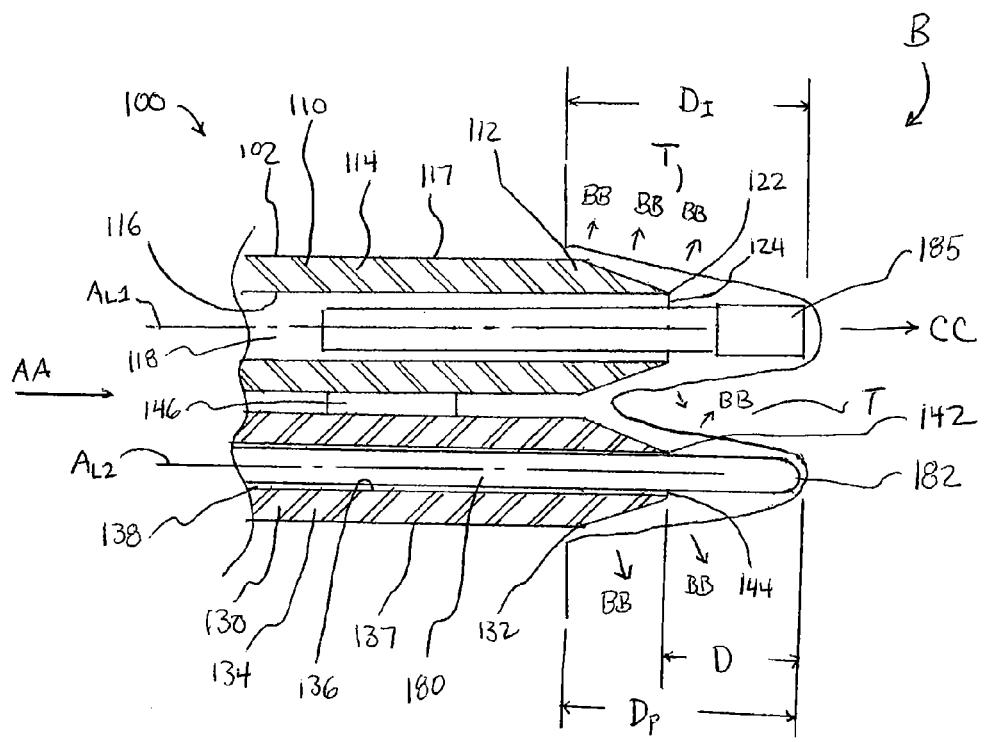

FIGS. 1 and 2 are schematic illustrations of a medical device 100 according to an embodiment of the invention in a first configuration and a second configuration, respectively. The medical device 100 includes an implant delivery device 102, a probe 180 and an elongate implant 185. The implant delivery device 102 has a first tubular member 110 and a second tubular member 130 coupled to the first tubular member 110 by a coupling member 146. The coupling member 146 can be any suitable coupling member such as, for example, a mechanical fastener, an adhesive fastener, a magnetic coupler or the like. Although the second tubular member 130 is shown as being coupled to the first tubular member 110 such that the second tubular member 130 is spaced apart from the first tubular member 110, in other embodiments, at least a portion of the second tubular member 130 can be coupled to and in contact with at least a portion of the first tubular member 110.

The first tubular member 110 defines a longitudinal axis $A_{L1}$ and has a proximal end portion (not shown in FIGS. 1 and 2) and a distal end portion 112. The first tubular member 110 includes a side wall 114 having an outer surface 117 and an inner surface 116. The inner surface 116 defines a lumen 118 that is substantially coaxial with the longitudinal axis $A_{L1}$. The lumen 118 is configured to receive an elongate implant 185, which can be, for example, an electrode, an electronic lead, a sensor or the like.

At least a portion of the distal end portion 112 of the first tubular member 110 is tapered along the longitudinal axis $A_{L1}$. Said another way, the height $H_1$ of the first tubular member 110 at a distal-most point (or locus of points) 122 is less than the height $H'_1$ of the first tubular member 110 at a point spaced proximally from the distal-most point (or locus of points) 122. Similarly stated, in embodiments in which the first tubular member 110 is cylindrically shaped, a diameter of the outer surface 117 of the first tubular member 110 decreases along the longitudinal axis $A_{L1}$ in a distal direction. In this manner, as described in more detail herein, when the medical device 100 is inserted into a patient's body B (see FIG. 2), the distal end portion 112 of the first tubular member 110 can dilate a bodily tissue T.

The distal end portion 112 of the first tubular member 110 defines an opening 124 in fluid communication with the lumen 118. In this manner, when the medical device 100 is disposed within a patient's body B, a portion of the elongate implant 185 can be conveyed from the lumen 118 into the patient's body B through the opening 124. Said another way, when the medical device 100 is disposed within a patient's body B, the elongate implant 185 can be moved within the lumen 118 of the first tubular member 110, through the opening 124, and into the patient's body B.

The second tubular member 130 defines a longitudinal axis $A_{L2}$ and has a proximal end portion (not shown in FIGS. 1 and 2) and a distal end portion 132. The second tubular member 130 is coupled to the first tubular member 110 such that the longitudinal axis $A_{L2}$ of the second tubular member 130 is substantially parallel to the longitudinal axis $A_{L1}$ of the first tubular member 110. The second tubular member 130 includes a side wall 134 having an outer surface 137 and an inner surface 136. The inner surface 136 of the second tubular member 130 defines a lumen 138 that is substantially coaxial with the longitudinal axis $A_{L2}$. The lumen 138 is configured to receive a probe 180, which can be, for example, an electronic targeting probe, a radio-opaque targeting probe, a guide wire or the like.

At least a portion of the distal end portion 132 of the second tubular member 130 is tapered along the longitudinal axis $A_{L2}$. Said another way, the height $H_2$ of the second tubular member 130 at a distal-most point (or locus of points) 142 is less than the height $H'_2$ of the second tubular member 130 at a point spaced proximally from the distal-most point (or locus of points) 142. Similarly stated, in embodiments in which the second tubular member 130 is cylindrically shaped, a diameter of the outer surface 137 of the second tubular member 130 decreases along the longitudinal axis $A_{L2}$ in a distal direction. In this manner, as described in more detail herein, when the medical device 100 is inserted into a patient's body B (see FIG. 2), the distal end portion 132 of the second tubular member 130 can dilate a bodily tissue T.

The distal end portion 132 of the second tubular member 130 defines an opening 144 in fluid communication with the lumen 138. In this manner, a distal end portion 182 of the probe 180 can extend from the lumen 138 into the patient's body B through the opening 144 to a depth $D_P$ without the distal end portion 112 of the first tubular member 110 and/or the distal end portion 132 of the second tubular member 130 being disposed within the body B. In some embodiments, the second tubular member 130 can be moved relative to the probe 180 such that the distal end portion 112 of the first tubular member 110 and/or the distal end portion 132 of the second tubular member 130 can be disposed into the patient's body B while the probe 180 remains in the patient's body at depth $D_P$. Said another way, in some embodiments, the probe 180 can be moved within the lumen 138 such that the implant insertion device 102 can be moved about the probe 180 and into the body B. In other embodiments, distal end portion 182 of the probe 180 can be retracted from the patient's body B through the opening 144.

As shown in FIG. 1, when the medical device 100 is in the first configuration, the probe 180 is disposed within the lumen 138 such that the distal end portion 182 of the probe 180 is disposed outside of the opening 144. Said another way, when the medical device 100 is in the first configuration, the distal end portion 182 of the probe 180 is spaced distally apart from the distal-most point (or locus of points) 142 of the second tubular member 130. In this manner, the distal end portion 182 of the probe 180 can be inserted first into the patient's body B. In some embodiments, for example, the probe 180 can be inserted percutaneously through an incision in the skin. More particularly, when the medical device is in the first configuration, the probe 180 can be inserted into the patient's body B to a depth $D_P$ without the distal end portion 112 of the first tubular member 110 and/or the distal end portion 132 of the second tubular member 130 being disposed within the body B. In this manner, the probe 180 can be used to target the placement of the implant delivery device 102 within the patient's body B. Said another way, the probe 180 can be used to ensure that the implant delivery device 102 is positioned at a predetermined location (e.g., proximate a particular anatomical structure, at a desired depth or the like) within the patient's body B.

When the medical device 100 is in the first configuration, the elongate implant 185 is disposed within the lumen 118 of the first tubular member 110 such that the elongate implant 185 does not extend outside of the opening 124. In this manner, the side wall 114 of the first tubular member 110 can prevent the elongate implant 185 from contacting portions of the patient's body B during insertion. Said another way, when the medical device 100 is in the first configuration, the side wall 114 of the first tubular member 110 can prevent the elongate implant 185 from being damaged during insertion.

When the distal end portion 182 of the probe 180 is positioned within the patient's body B as desired, the implant delivery device 102 can be moved relative to the probe 180, as shown by the arrow AA in FIG. 2, such that the distal end portion 112 of the first tubular member 110 and the distal end portion 132 of the second tubular member 130 are disposed within the patient's body B. Said another way, the lumen 138 of the second tubular member 130 is moved distally about the probe 180 until the distal end portion 182 of the probe 180 is spaced apart distally from the distal-most point (or locus of points) 142 of the second tubular member 130 by a predetermined distance D. In this manner, the insertion of the medical device 100 is guided by the probe 180. In some embodiments, for example, the implant delivery device 102 can be inserted into the patient's body B percutaneously through an incision in the skin.

When the medical device 100 is inserted into the patient's body B, as described above, the distal end portion 112 of the first tubular member 110 and/or the distal end portion 132 of the second tubular member 130 can dilate the bodily tissue T, as shown by the arrows BB in FIG. 2. After the medical device 100 is inserted to the desired depth within the body B, at least a portion of the elongate implant 185 can be conveyed from the lumen 118 of the first tubular member 110 into the patient's body B through the opening 124, as shown by the arrow CC. In some embodiments, the elongate implant 185 can be positioned within the body B at a depth $D_1$ that is substantially the same as the depth $D_P$ of the probe 180. In other embodiments, the elongate implant 185 can be positioned within the body B at a depth $D_1$ that is different from the depth $D_P$ of the probe 180 by a predetermined distance. In this manner, after the desired insertion depth and/or location is determined by the probe 180, the medical device 100 can deliver the elongate implant 185 into the body B at the desired insertion depth and/or location. After the elongate implant 185 is conveyed from the lumen 118 of the first tubular member 110, the medical device 100 can be removed from the patient's body B. Although only the distal end portion of the elongate implant 185 is shown as being conveyed from the lumen 118, in other embodiments, the entire elongate implant 185 can be conveyed from the lumen 118.

Although the height of the distal end portion 112 of the first tubular member 10 is shown as changing along the longitudinal axis $A_{L1}$ (e.g., $H_1$ to $H'_1$), in some embodiments, a depth (i.e., a dimension normal to the height and normal to the longitudinal axis $A_{L1}$) of the distal end portion 112 of the first tubular member 110 can decrease along the longitudinal axis $A_{L1}$ in a distal direction. In other embodiments, both the height and the depth of the distal end portion 112 of the first tubular member 110 can decrease along the longitudinal axis $A_{L1}$ in a distal direction. Said another way, in some embodiments, the distal end portion 112 of the first tubular member 110 can be tapered along the longitudinal axis $A_{L1}$ in two dimensions. Similarly, although the height of the distal end portion 132 of the second tubular member 130 is shown as changing along the longitudinal axis $A_{L2}$ (e.g., $H_2$ to $H'_2$), in some embodiments, a depth (i.e., a dimension normal to the height and normal to the longitudinal axis $A_{L2}$) of the distal end portion 132 of the second tubular member 130 can decrease along the longitudinal axis $A_{L2}$ in a distal direction. In other embodiments, both the height and the depth of the distal end portion 132 of the second tubular member 130 can decrease along the longitudinal axis $A_{L2}$ in a distal direction. Said another way, in some embodiments, the distal end portion 132 of the second tubular member 130 can be tapered along the longitudinal axis $A_{L2}$ in two dimensions.

Although the distal end portion 112 of the first tubular member 110 and the distal end portion 132 of the second tubular member 130 are shown as being tapered symmetrically along the longitudinal axes $A_{L1}$ and $A_{L2}$, respectively, in other embodiments, the distal end portion 112 of the first tubular member 110 and/or the distal end portion 132 of the second tubular member 130 can be tapered asymmetrically along the longitudinal axes $A_{L1}$ and $A_{L2}$, respectively. Said another way, in some embodiments, the distal end portion 112 of the first tubular member 110 and/or the distal end portion 132 of the second tubular member 130 can be beveled.

Figure 3:
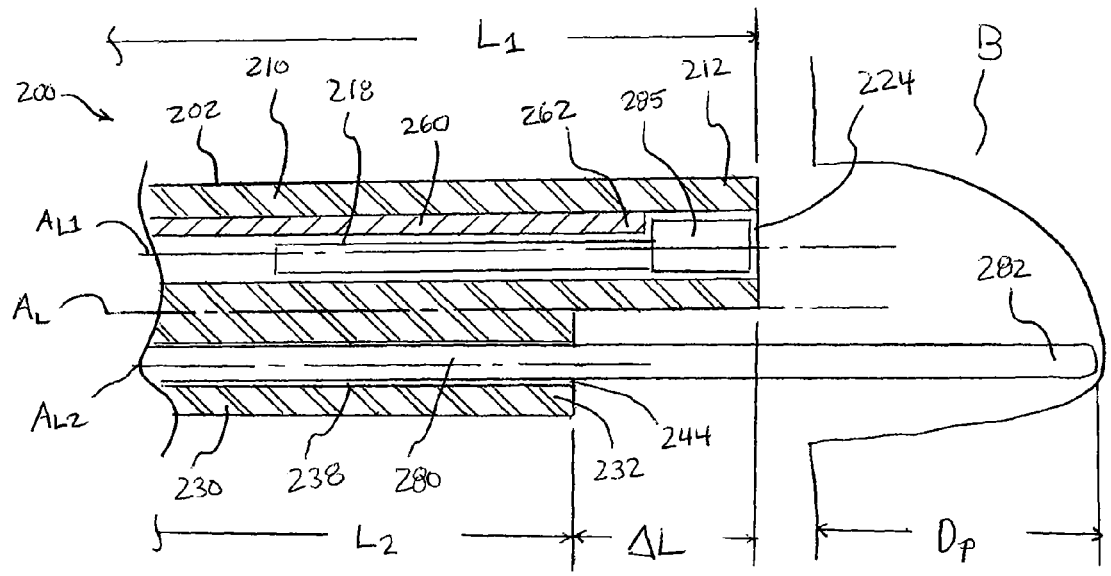
FIGS. 3-5 are schematic illustrations of a medical device according to an embodiment of the invention in a first configuration, a second configuration and a third configuration, respectively.
Figure 4:
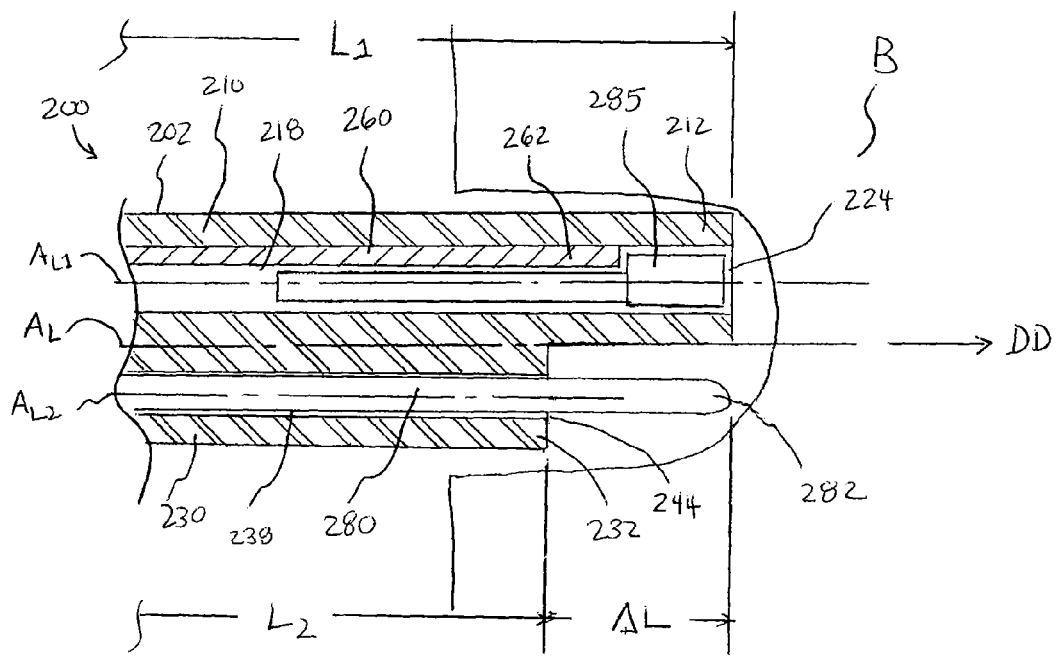

Similarly, although the distal end portion 112 of the first tubular member 110 and the distal end portion 132 of the second tubular member 130 are shown as being tapered along the longitudinal axes $A_{L1}$ and $A_{L2}$, respectively, in other embodiments, the distal end portion 112 of the first tubular member 110 and/or the distal end portion 132 of the second tubular member 130 need not be tapered. For example, FIGS. 3 and 4 are schematic illustrations of a medical device 200 according to an embodiment of the invention in a first configuration and a second configuration, respectively. The medical device 200 includes an implant delivery device 202, a retention member 260, a probe 280 and an elongate implant 285.

The implant delivery device 202 has a first portion 210 and a second portion 230 and defines a longitudinal axis $A_{L1}$. The first portion 210 of the implant delivery device 202 has a proximal end portion (not shown in FIGS. 3 and 4) and a distal end portion 212. The first portion 210 of the implant delivery device 202 defines a lumen 218 having a longitudinal axis $A_{L1}$ that is substantially parallel with the longitudinal axis $A_L$ of the implant delivery device 202. The lumen 218 of the first portion 210 is configured to receive an elongate implant 285, which can be, for example, an electrode, an electronic lead, a sensor or the like. The distal end portion 212 of the first portion 210 defines an opening 224 in fluid communication with the lumen 218. In this manner, when the medical device 200 is disposed within a patient's body B, at least a portion of the elongate implant 285 (e.g., the distal end portion) can be conveyed from the lumen 218 into the patient's body B through the opening 224.

The retention member 260 has a proximal end portion (not shown in FIGS. 3 and 4) and a distal end portion 262. The retention member 260 is movably disposed within the lumen 218 of the first portion 210 such that its distal end portion 262 is adjacent to the elongate implant 285. In some embodiments, the retention member 260 can contact and/or engage a portion of the elongate implant 285. In this manner, the retention member 260 can limit the movement of the elongate implant 285 within the lumen 218 of the first portion 210. For example, in some embodiments, the retention member 260 can limit the movement of the elongate implant 285 within the lumen 218 in a proximal direction. In other embodiments, the retention member 260 can move within the lumen 218 of the first portion 210 thereby causing the elongate implant 285 to move within the lumen 218 and/or out of the lumen 218 through the opening 224.

The second portion 230 of the implant delivery device 202 has a proximal end portion (not shown in FIGS. 3 and 4) and a distal end portion 232. The second portion 230 of the implant delivery device 202 defines a lumen 238 having a longitudinal axis $A_{L2}$ that is substantially parallel with the longitudinal axis $A_L$ of the implant delivery device 202 and the longitudinal axis $A_{L1}$ of the lumen 218. The lumen 238 is configured to receive a probe 280, which can be, for example, an electronic targeting probe, a radio-opaque targeting probe, a guide wire or the like. The distal end portion 232 of the second portion 230 defines an opening 244 in fluid communication with the lumen 238. In this manner, at least a distal end portion 282 of the probe 280 can extend from the lumen 238 into the patient's body B through the opening 244.

The first portion 210 of the implant delivery device 202 has a longitudinal length $L_1$. The second portion 230 of the implant delivery device 202 has a longitudinal length $L_2$ that is less than the longitudinal length $L_1$ of the first portion 210. In this manner, when the proximal end (not shown) of the first portion 210 and the proximal end (not shown) of the second portion 230 are longitudinally aligned (i.e., disposed at the same longitudinal position), the distal end portion 232 of the second portion 230 is spaced apart proximally from the distal end portion 212 of the first portion 210. Said another way, the first portion 210 is disposed relative to the second portion 230 such that the distal end portion 212 of the first portion 230 extends distally from the distal end portion 232 of the second portion 230 by a distance ΔL.

As shown in FIG. 3, when the medical device 200 is in the first configuration, the probe 280 is disposed within the lumen 238 of the second portion 230 such that the distal end portion 282 of the probe 280 is disposed outside of the opening 244. In this manner, the distal end portion 282 of the probe 280 can be inserted into the patient's body B to a depth $D_P$ without the distal end portion 212 of the first portion 210 of the implant delivery device 202 and/or the distal end portion 232 of the second portion 230 of the implant delivery device 202 being disposed within the body B. Said another way, the probe 280 can be used to target the placement of the implant delivery device 202 within the patient's body. Said yet another way, the probe 280 can be used to ensure that the implant delivery device 202 is positioned at a predetermined location (e.g., proximate a particular anatomical structure, at a desired depth or the like) within the patient's body B. In some embodiments, the distal end portion 282 of the probe 280 can be inserted into the patient's body B to a depth $D_P$ such that the distal end portion 212 of the first portion 210 and/or the distal end portion 232 of the second portion 230 is being disposed within the body B.

When the distal end portion 282 of the probe 280 is positioned within the patient's body B as desired, the implant delivery device 202 can be moved distally relative to the probe 280, as shown by the arrow DD in FIG. 4, thereby placing the medical device in its second configuration. Said another way, the lumen 238 of the second portion 230 is moved distally about the probe 280 until the distal end portion 282 of the probe 280 is longitudinally aligned with the distal end portion 212 of the first portion 210. Said yet another way, the lumen 238 of the second portion 230 is moved distally about the probe 280 until the distal end portion 282 of the probe 280 extends from the distal end portion 232 of the second portion 230 by the distance ΔL. In other embodiments, however, the lumen 238 of the second portion 230 is moved distally about the probe 280 until the distal end portion 282 of the probe 280 extends from the distal end portion 232 of the second portion 230 by a different distance than the distance ΔL. Accordingly, when the medical device 200 is in the second configuration, at least the distal end portion 212 of the first portion 210 is disposed within the patient's body B at a desired depth and/or location.

Figure 5:
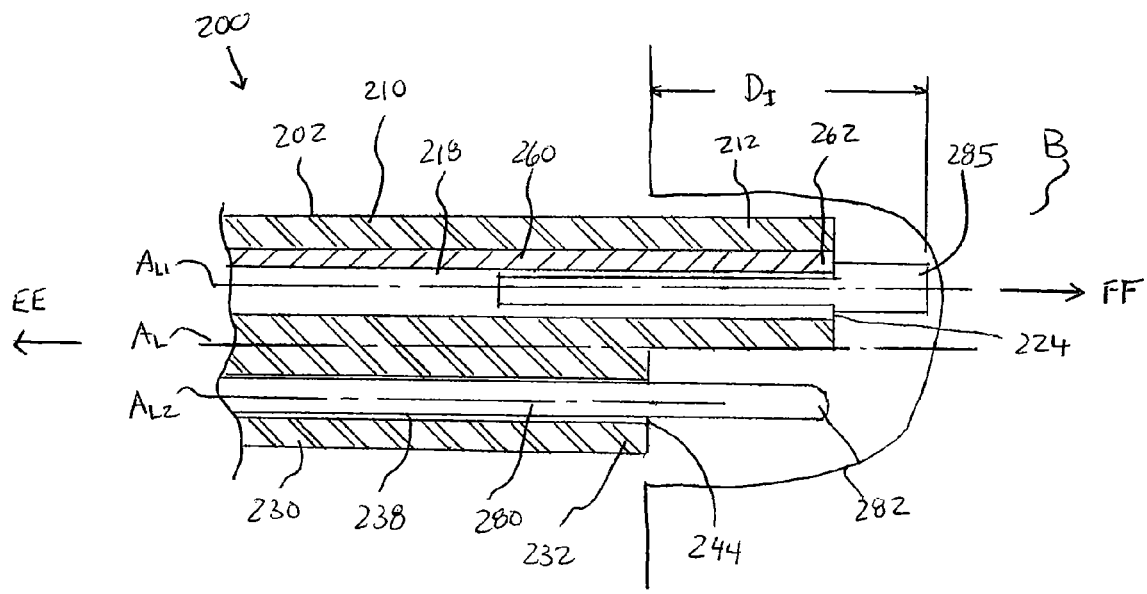

After the distal end portion 212 of the first portion 210 is disposed within the patient's body B at the desired depth and/or location, the implant delivery device 202 can be moved relative to the retention member 260 and the elongate implant 285, as shown by the arrow EE in FIG. 5, thereby placing the medical device 200 in its third configuration. Said another way, the first portion 210 is moved proximally about the retention member 260 such that the distal end portion 262 of the retention member 260 contacts and/or engages the elongate implant 285. In this manner, the retention member 260 limits the movement of the elongate implant 285 within the lumen 218 of the first portion 210 and/or limits the movement of the elongate implant 285 relative to the body B. Accordingly, continued proximal movement of the first portion 210 causes at least a portion of the elongate implant 285 to be conveyed from the lumen 218 and into the body B through the opening 224, as shown by the arrow FF.

Moreover, because the retention member 260 limits the movement of the elongate implant 285 relative to the body B, the elongate implant 285 is implanted in the patient's body B at a depth $D_1$ that is substantially the same as the depth $D_P$. In this manner, the depth and/or location of the elongate implant 285 can be guided by the probe 280. In other embodiments, however, the retention member 260 can move within the lumen 218 (e.g., relative to the implant delivery device 202 to move the elongate implant 285 either distally or proximally relative to the patient's body B. In such embodiments, the elongate implant 285 is implanted in the patient's body B at a depth $D_1$ different than the depth $D_P$.

Although the probe 280 is shown as moving with the implant delivery device 202 when the implant delivery device is moved to its third configuration (e.g., FIG. 5), in other embodiments, the probe 280 can remain disposed in the patient's body B at the depth $D_P$. Said another way, when the medical device 200 is moved from its second configuration to its third configuration, the probe 280 can move relative to the second portion 230 of the implant delivery device 202 within the lumen 238. In yet other embodiments, the probe 280 can be entirely removed from the implant delivery device 202 after the medical device is in its second configuration.

Figure 6:
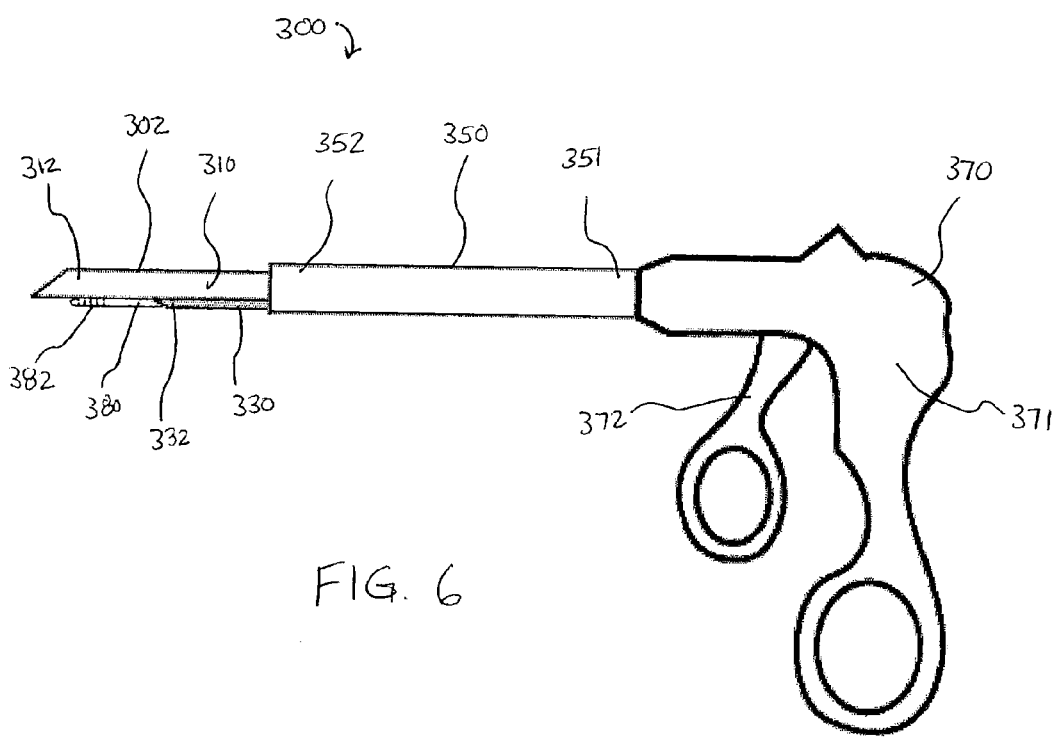
FIG. 6 is a side view of a medical device according to an embodiment of the invention.
Figure 7:
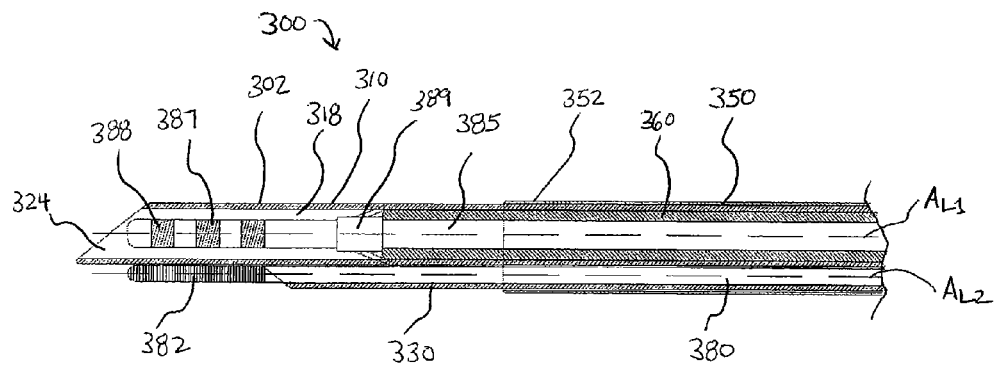
FIG. 7 is a side cross-sectional view of the distal portion of the medical device shown in FIG. 6.
Figure 8:
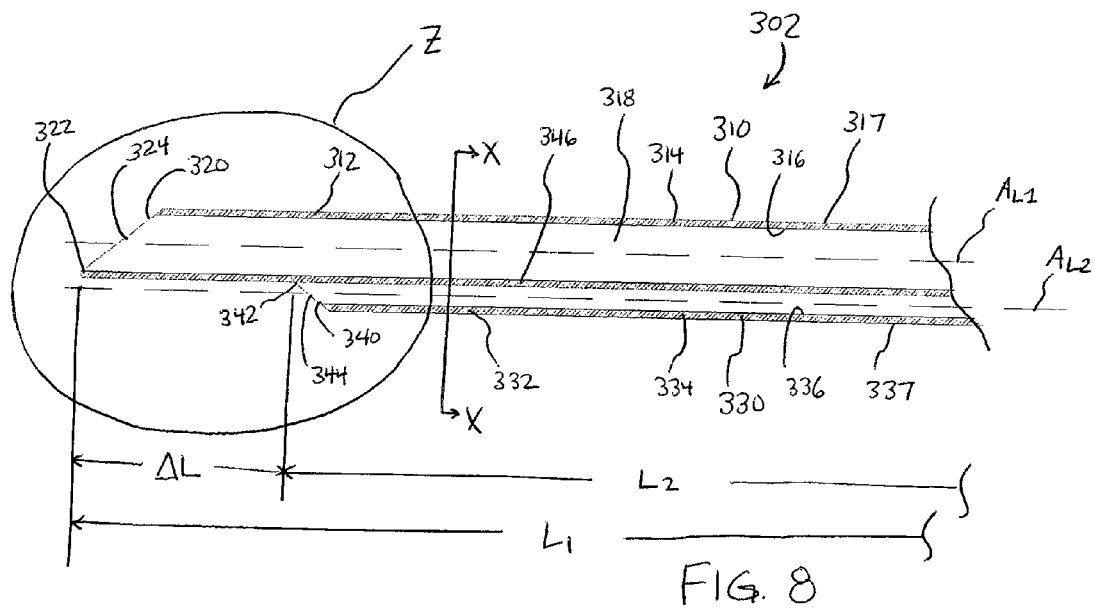
FIG. 8 is a side cross-sectional view of a portion of the medical device shown in FIG. 6.

FIGS. 6 and 7 show a side view and a partial cross-sectional side view, respectively, of a medical device 300 according to an embodiment of the invention. The medical device 300 includes an implant delivery device 302, a retention member 360 (see FIG. 7), a sheath 350, an actuator 370, a probe 380 and an elongate implant 385 (see FIG. 7). The elongate implant 385 and the probe 380 are each movably disposed within the implant delivery device 302. The retention member 360 is movably disposed within the implant delivery device 302 and is configured to selectively retain the elongate implant 385 within the implant delivery device 302. At least a portion of the implant delivery device 302 is movably disposed within the sheath 350. The proximal end portion 351 of the sheath 350 and/or the proximal end portion (not shown in FIGS. 6 and 7) of the implant delivery device 302 are coupled to the actuator 370. A detailed description of these components is provided below with respect to FIGS. 8-17.

As shown in FIGS. 8-11, the implant delivery device 302 has a first tubular member 310 defining a longitudinal axis $A_{L1}$ and a second tubular member 330 defining a longitudinal axis $A_{L2}$. The first tubular member 310 is coupled to the second tubular member 330 such that the longitudinal axis $A_{L1}$ is substantially parallel to the longitudinal axis $A_{L2}$. Similarly stated, first tubular member 310 is coupled to the second tubular member 330 longitudinally along an interface portion 346. The interface portion 346 defines a coupling line L (see FIG. 11) that is substantially parallel to the longitudinal axis $A_{L1}$ and the longitudinal axis $A_{L2}$. Similarly stated, an outer surface 317 of the first tubular member 310 and an outer surface 337 of the second tubular member 330 are coupled together such that they collectively define the coupling line L. Although the first tubular member 310 and the second tubular member 330 are described as being two separate components coupled together, in other embodiments, the first tubular member 310 and the second tubular member 330 can be monolithically formed.

Figure 9:
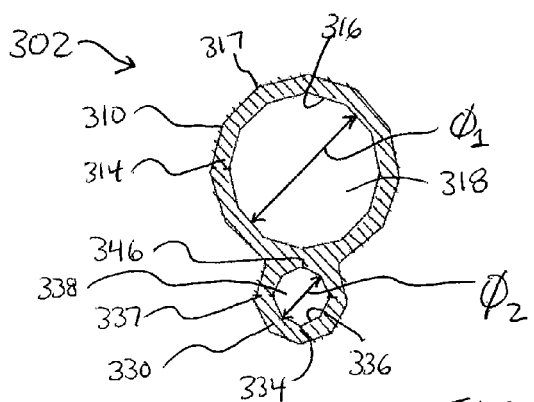
FIG. 9 is a cross-sectional view of the portion of the medical device shown in FIG. 7 taken along line X-X in FIG. 8.

The first tubular member 310 has a proximal end portion (not shown in FIGS. 8-11) and a distal end portion 312. The first tubular member 310 includes a side wall 314 having the outer surface 317 and an inner surface 316. The inner surface 316 defines a lumen 318 that is substantially coaxial with the longitudinal axis $A_{L1}$. The lumen 318 is configured to receive an elongate implant 385, which can be, for example, an electrode, an electronic lead, a sensor or the like. As shown in FIG. 9, the lumen 318 of the first tubular member 310 has a diameter $\phi_1$. In other embodiments, the lumen 318 and/or the side wall 314 can have a non-circular cross-sectional shape, such as, for example, an elliptical shape.

Figure 10:
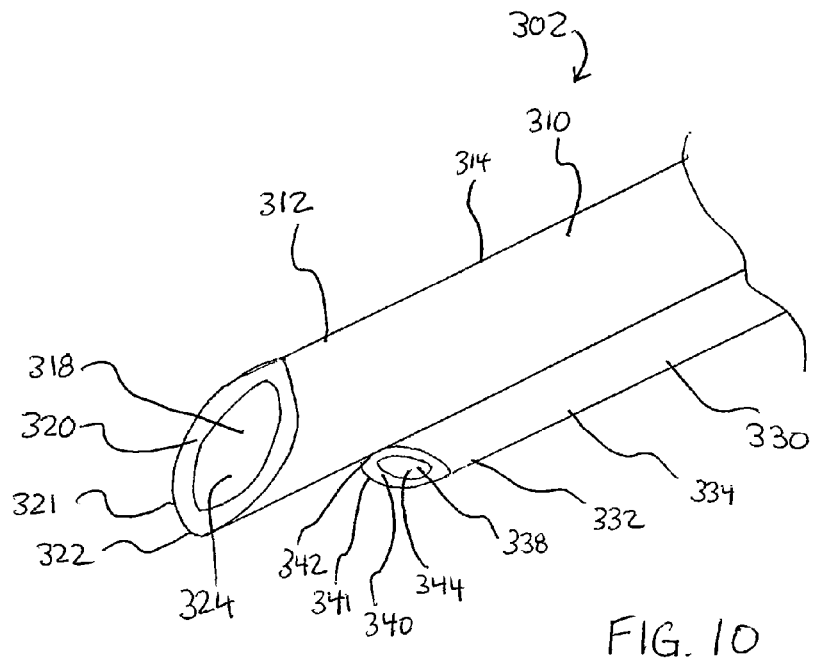
FIG. 10 is a perspective view of the portion of the medical device shown in FIG. 7.

The distal end portion 312 of the first tubular member 310 includes a distal end surface 320 that is tapered asymmetrically along the longitudinal axis $A_{L1}$. Said another way, the distal end portion 312 of the first tubular member 310 is beveled such that the distal end surface 320 is oblique. Accordingly, the distal end surface 320 of the first tubular member 310 includes an edge 321 having a distal-most point (or tip) 322. Additionally, because the distal end portion 312 is beveled, the distal end surface 320 has a non-circular shape (e.g., an elliptical shape as shown in FIG. 10). Moreover, the beveled arrangement of the distal end portion 312 is such that the edge 321 has a substantially continuous shape and is devoid of a sharp point. Said another way, the edge 321 and the distal-most point 322 collectively form a blunt tip. In this manner, as described in more detail herein, when the medical device 300 is inserted into a patient's body, the distal end portion 312 of the first tubular member 310 can dilate, displace and/or stretch a bodily tissue without piercing or cutting the tissue.

Figure 11:
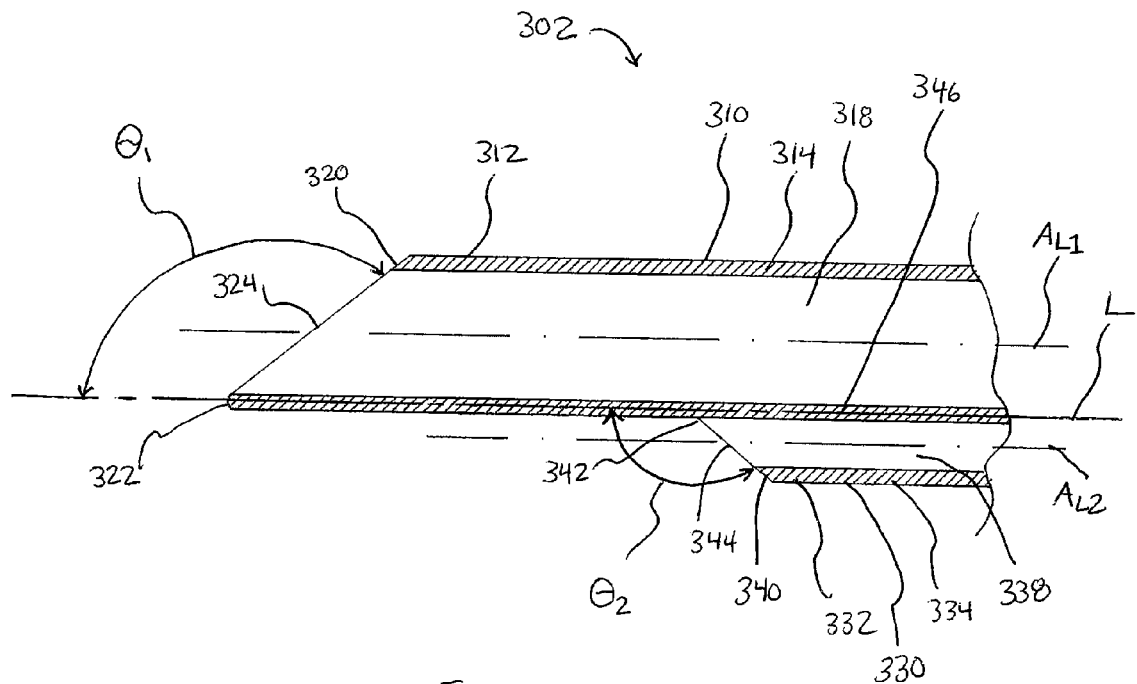
FIG. 11 is a side cross-sectional view of a portion of the medical device shown in FIG. 7 labeled as Z in FIG. 7.

As shown in FIG. 11, the distal end surface 320 and the coupling line L as it extends distally from the distal end surface 320 of the first tubular member 310 collectively define an angle $\Theta_1$ that is greater than ninety degrees. Said another way, the coupling line L includes the distal-most point 322 of the distal end surface 320. Said yet another way, the distal end portion 312 of the first tubular member 310 is tapered and/or beveled away from the coupling line L. In this manner, as described in more detail herein, the distal end portion 312 of the first tubular member 310 can dilate, displace and/or stretch the bodily tissue in a predetermined direction and/or orientation.

The distal end surface 320 of the first tubular member 310 defines an opening 324 in fluid communication with the lumen 318. In this manner, the elongate implant 385 can be conveyed from the lumen 318 into the patient's body B through the opening 324. Said another way, when the medical device 300 is disposed within a patient's body, the elongate implant 385 can be moved within the lumen 318 of the first tubular member 310, through the opening 324, and into the patient's body.

The second tubular member 330 has a proximal end portion (not shown in FIGS. 8-11) and a distal end portion 332. The second tubular member 330 includes a side wall 334 having the outer surface 337 and an inner surface 336. The inner surface 336 of the second tubular member 330 defines a lumen 338 that is substantially coaxial with the longitudinal axis $A_{L2}$. The lumen 338 is configured to receive a probe 380, which can be, for example, an electronic targeting probe, a radio-opaque targeting probe, a guide wire or the like. As shown in FIG. 9, the lumen 338 of the second tubular member 330 has a diameter $\phi_2$. In other embodiments, the lumen 338 and/or the side wall 334 can have a non-circular cross-sectional shape, such as, for example, an elliptical shape. Although the diameter $\phi_2$ is shown as being smaller than the diameter $\phi_1$, in other embodiments, the diameter $\phi_2$ can be equal to or greater than the diameter $\phi_1$.

The distal end portion 332 of the second tubular member 330 includes a distal end surface 340 that is tapered asymmetrically along the longitudinal axis $A_{L2}$. Said another way, the distal end portion 332 of the second tubular member 330 is beveled such that the distal end surface 340 is oblique. Accordingly, the distal end surface 340 of the second tubular member 330 includes an edge 341 having a distal-most point (or tip) 342. Additionally, because the distal end portion 332 is beveled, the distal end surface 340 has a non-circular shape (e.g., an elliptical shape as shown in FIG. 10). Moreover, the beveled arrangement of the distal end portion 332 of the second tubular member 330 is such that the edge 341 has a substantially continuous shape and is devoid of a sharp point. Said another way, the edge 341 and the distal-most point 342 collectively form a blunt tip. In this manner, as described in more detail herein, when the medical device 300 is inserted into a patient's body, the distal end portion 342 of the second tubular member 330 can dilate, displace and/or stretch a bodily tissue without piercing or cutting the tissue.

As shown in FIG. 11, the distal end surface 340 of the second tubular member 330 and the coupling line L as it extends distally from the distal end surface 340 of the second tubular member 330 collectively define an angle $\Theta_2$ that is greater than ninety degrees. Said another way, the coupling line L includes the distal-most point 342 of the second tubular member 330. Said yet another way, the distal end portion 332 of the second tubular member 330 is tapered and/or beveled away from the coupling line L. In this manner, as described in more detail herein, the distal end portion 332 of the second tubular member 330 can dilate, displace and/or stretch the bodily tissue in a predetermined direction and/or orientation. In some embodiments, the angle $\Theta_2$ of the second tubular member 330 is the same as the angle $\Theta_1$ of the first tubular member 310. In other embodiments, the angle $\Theta_2$ of the second tubular member 330 is the different from the angle $\Theta_1$ of the first tubular member 310.

The distal end surface 340 of the second tubular member 330 defines an opening 344 in fluid communication with the lumen 338. In this manner, at least a distal end portion 382 of the probe 380 can extend from the lumen 338 into the patient's body through the opening 344.

The first tubular member 310 of the implant delivery device 302 has a longitudinal length $L_1$. The second tubular member 330 of the implant delivery device 302 has a longitudinal length $L_2$ that is less than the longitudinal length $L_1$ of the first tubular member 310. In this manner, when the proximal end (not shown) of the first tubular member 310 and the proximal end (not shown) of the second tubular member 330 are longitudinally aligned (i.e., disposed at the same longitudinal position), the distal end tubular member 332 of the second tubular member 330 is spaced apart proximally from the distal end tubular member 312 of the first tubular member 310. Said another way, the first tubular member 310 is disposed relative to the second tubular member 330 such that the distal-most point 322 of the first tubular member 330 extends distally from the distal-most point 342 of the second tubular member 330 by a distance ΔL.

Figure 12:
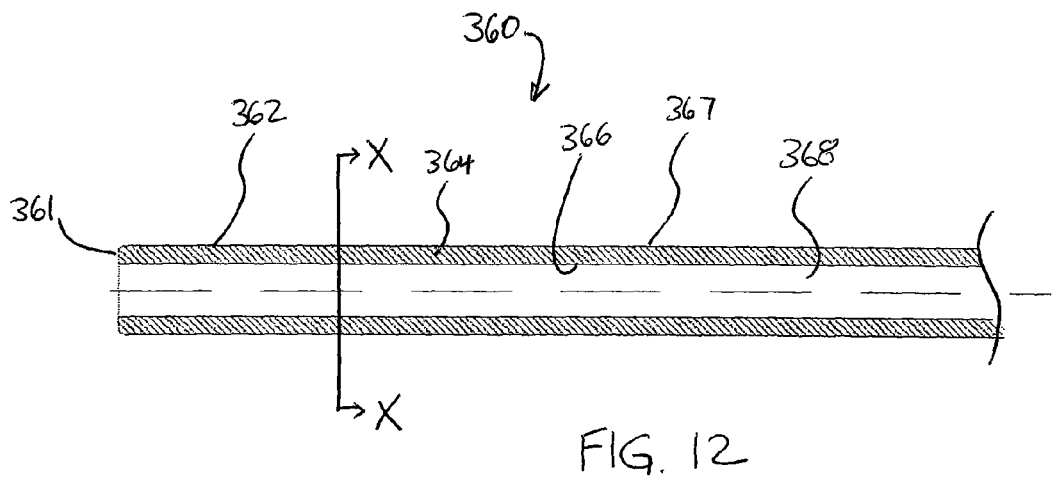
FIG. 12 is a side cross-sectional view of the retainer of the medical device shown in FIG. 6.
Figure 13:
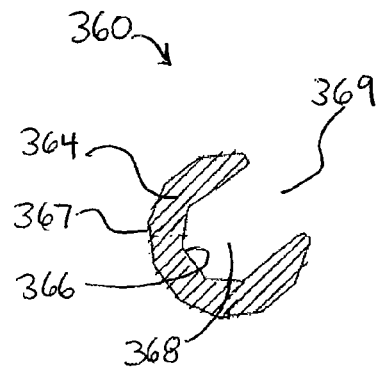
FIG. 13 is a cross-sectional view of the retainer of the medical device shown in FIG. 12 taken along line X-X in FIG. 12.

As shown in FIGS. 12 and 13, the retainer 360 has a distal end portion 362 having a distal end surface 361. The retainer 360 includes a side wall 364 having an outer surface 367 and an inner surface 366. The inner surface 366 defines a lumen 368 that is configured to receive a portion of the elongate implant 385. More particularly, when the elongate implant 385 is disposed within the lumen 368 of the retainer 360, the distal end surface 361 of the retainer 360 can contact and/or engage a shoulder 391 of an anchor portion 389 of the elongate implant 385. In this manner, the retainer 360 can limit the movement of the elongate implant 385 within the lumen 318 of the first tubular member 310. For example, in some embodiments, the retainer can limit the movement of the elongate implant 385 within the lumen 318 in a proximal direction. In other embodiments, the retainer 360 can move distally within the lumen 318 of the first tubular member 310 such that the distal end surface 361 of the retainer 360 moves the anchor portion 389 of the elongate implant 385 distally, thereby causing the elongate implant 385 to move within the lumen 318 and/or out of the lumen 318 through the opening 324.

As shown in FIG. 13, the side wall 364 of the retainer 360 defines a longitudinal opening 369. Said another way, the side wall 364 of the retainer 360 has a "C-shaped" cross-section. This arrangement allows the elongate implant 385 to be disposed within the lumen 368 of the retainer 360 from the side, rather than solely from an end portion of the retainer 360. After the elongate implant 385 is disposed within the retainer 360, the elongate implant 385 and the retainer 360 can collectively be disposed within the lumen 318 of the first tubular member 310 of the implant delivery device 302 (see e.g., FIG. 7). In other embodiments, the side wall 364 of the retainer 360 can be devoid of a longitudinal opening such that the retainer 360 has a circular cross-sectional shape.

Figure 14:
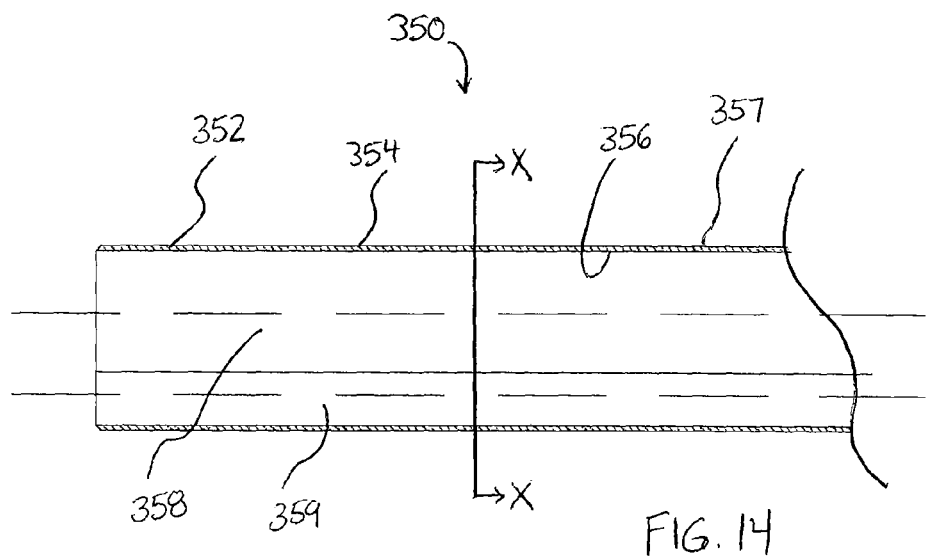
FIG. 14 is a side cross-sectional view of the sheath of the medical device shown in FIG. 6.
Figure 15:
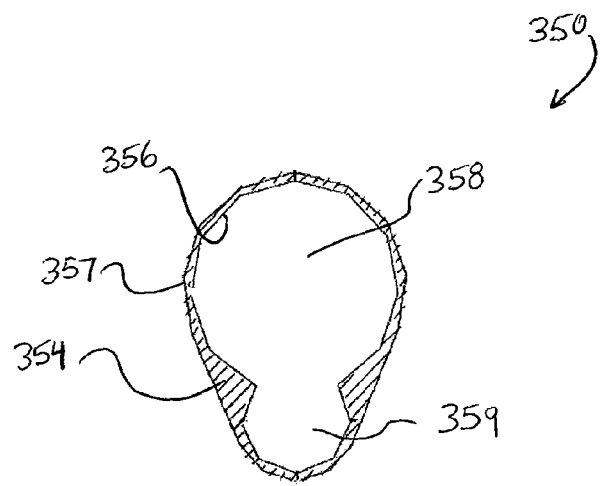
FIG. 15 is a cross-sectional view of the sheath of the medical device shown in FIG. 14 taken along line X-X in FIG. 14.

As shown in FIGS. 14 and 15, the sheath 360 has a proximal end portion 351 (see FIG. 6) and distal end portion 352. The sheath 350 includes a side wall 354 having an outer surface 357 and an inner surface 356. The inner surface 356 defines a first lumen 358 and a second lumen 359. The first lumen 358 is configured to be movably disposed about the first tubular member 310 of the implant delivery device 302. Said another way, the diameter (not shown in FIGS. 14 and 15) of the first lumen 358 of the sheath 350 is greater than the outer diameter (not shown in FIGS. 8-11) of the first tubular member 310 such that the first tubular member 310 can be moved within the first lumen 358. Similarly, the second lumen 359 is configured to be movably disposed about the second tubular member 330 of the implant delivery device 302. Said another way, the diameter (not shown in FIGS. 14 and 15) of the second lumen 359 of the sheath 350 is greater than the outer diameter (not shown in FIGS. 8-11) of the second tubular member 330 such that the second tubular member 330 can be moved within the second lumen 359. In this manner, the implant delivery device 302 can be movably disposed within the sheath 350. Although the first lumen 358 and the second lumen 359 are each shown as having a substantially circular cross-sectional shape, in other embodiments, the first lumen 358 and/or the second lumen 359 can have any suitable shape such that the implant delivery device 302 can be movably disposed within the sheath 350 as described above.

As shown in FIG. 6, the actuator 370 includes a handle 371 and a lever 372. The handle 371 is configured such that a user can manipulate the medical device 300 with one hand. The actuator 370 is coupled to the proximal end portion 351 of the sheath 350 and/or the proximal end portion (not shown in FIGS. 6 and 7) of the implant delivery device 302 such that movement of the lever 372 relative to the handle 371 causes the implant delivery device 302 to move relative to the sheath 350. More particularly, In this manner, as described herein, the elongate implant 385 can be conveyed from the lumen 318 of the first tubular member 310 into the patient's body. In some embodiments, the actuator 370 can include a ratchet mechanism, a detent, or the like to selectively move the implant delivery device 302 relative to the sheath 350.

Figure 16:
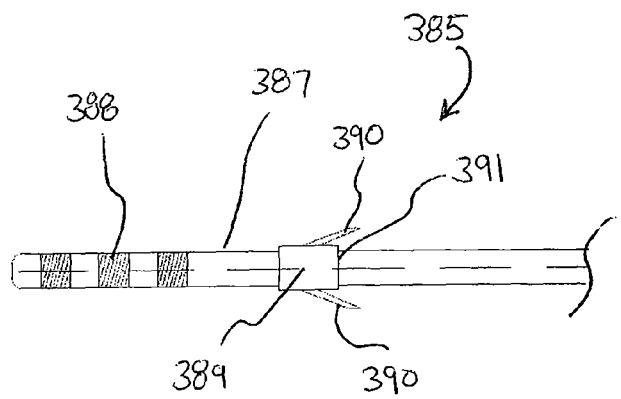
FIG. 16 is a side view of a portion of the elongate implant of the medical device shown in FIG. 7.

As shown in FIG. 16, the elongate implant 385 has a distal end portion 387 that includes an electrode array 388 and an anchoring portion 389. The electrode array 388 includes at least one electrode configured to electrically stimulate a target tissue, such as, for example, nervous tissue. In some embodiments, for example, the electrode array 388 can be configured to stimulate peripheral nerves, spinal roots and/or other structures near the central nervous system. In other embodiments, the electrode array 388 can stimulate a bodily organ or tissue, such as for example a muscle, a nerve, a heart or the like. In yet other embodiments, the electrode array 388 can include at least one electrode configured to receive an electronic signal produced by the body. For example, in some embodiments, the electrode array 388 can be configured to receive electronic signals to record activity of the nervous system.

The anchoring portion 389 includes a shoulder 391 and at least one flexible tine 390. As described in more detail herein, the flexible tines 390 are configured to move and/or deform when the elongate implant 385 is conveyed from the lumen 318 of the first tubular member 310 into the patient's body such that the flexible tines 390 can retain the elongate implant 385 within the patient's body. Said another way, the flexible tines 390 are configured to move and/or deform to engage a bodily tissue when the elongate implant 385 is inserted into the patient's body to maintain a location of the electrode array 388 within the patient's body. As described above, the shoulder 391 of the anchoring portion 389 is configured to contact and/or engage the distal end surface 361 of the retainer 360 such that the retainer 360 can limit movement of the elongate implant 385 within the lumen 318 of the first tubular member 310.

Figure 17:
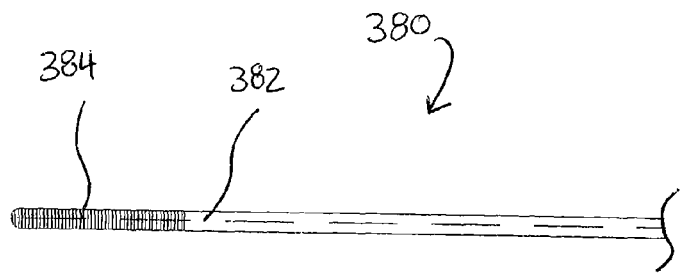
FIG. 17 is a side view of a portion of the probe of the medical device shown in FIG. 7.

As shown in FIG. 17, the probe 380 has a distal end portion 382 that includes an electrode 384. Similar to the electrode array 388 of the elongate implant 385, the electrode 384 of the probe 380 is configured to electrically stimulate a target tissue, such as, for example, nervous tissue. In some embodiments, for example, the electrode 384 can be configured to stimulate peripheral nerves, spinal roots and/or other structures near the central nervous system. In other embodiments, the electrode 384 can stimulate a bodily organ. In yet other embodiments, the electrode 384 can be configured to receive an electronic signal produced by the body. In this manner, as described in more detail herein, the probe 380 can be used to stimulate a target tissue and/or receive a signal from a target tissue to target the placement of the implant delivery device 302 within the patient's body. Said another way, the probe 380 can be used to ensure that the implant delivery device 302 is positioned at a predetermined location (e.g., proximate a particular anatomical structure, at a desired depth or the like) within the patient's body.

Figure 18:
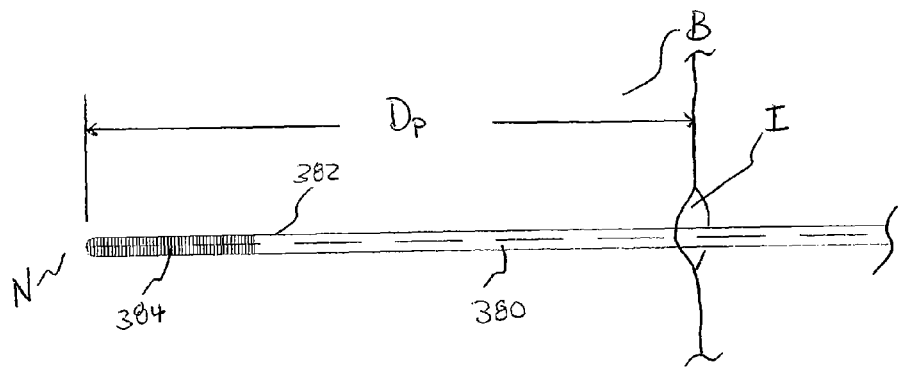
FIG. 18 is a side view of a portion of the probe of the medical device shown in FIG. 7 disposed within a patient's body.

The operation of the medical device 300 is discussed below with reference to FIGS. 18-22, which are cross-sectional views of the distal end portion of the medical device 300 in various configurations. As shown in FIG. 18, when the medical device 300 is in the first configuration, the probe 380 is disposed apart from the implant delivery device 302. Accordingly, the distal end portion 382 of the probe 380 can be inserted into the patient's body B to a desired depth $D_P$ and/or location without requiring the manipulation of the implant delivery device 302. In some embodiments, the probe 380 can be inserted percutaneously through an incision I in the skin. In this manner, the user can iteratively test the suitability of various locations within the patient's body B before inserting the implant delivery device 302. For example, in some embodiments, the user can stimulate a bodily tissue via the electrode 384 of the probe 380 to locate the desired target N, which can be, for example, a nerve, a muscle or the like. Said another way, the probe 380 can be used to target the placement of the implant delivery device 302 within the patient's body B. Said yet another way, the probe 380 can be used to ensure that the implant delivery device 302 is positioned at a predetermined location (e.g., proximate a particular anatomical structure, at a desired depth or the like) within the patient's body B.

When the distal end portion 382 of the probe 380 is positioned within the patient's body B as desired, the implant delivery device 302 can be placed about the probe 380 such that a portion of the probe 380 is disposed within the lumen 338 of the second tubular member 330. The implant delivery device 302 can then be moved distally relative to the probe 380, as shown by the arrow GG in FIG. 19, thereby placing the medical device 300 in its second configuration. Said another way, the lumen 338 of the second tubular member 330 is moved distally about the probe 380 until the distal end portion 382 of the probe 380 is longitudinally aligned with the distal end portion 312 of the first tubular member 310 and/or the distal end portion 387 of the elongate implant 385. In this manner, the elongate implant 385 can be inserted into the patient's body B at a depth $D_1$ that is substantially the same as the depth $D_P$. Accordingly, when the medical device 300 is in the second configuration, at least the distal end portion 312 of the first tubular member 310 is disposed within the patient's body B such that the electrode array 388 of the elongate implant 385 is at a desired depth and/or location within the patient's body B.

In some embodiments, when the implant delivery device 302 is placed about the probe 380, the proximal end portion of the probe 380 can extend proximally from the actuator 370. Moreover, the proximal end portion of the probe 380 and/or the actuator 370 can include an indexing mechanism (not shown in FIGS. 18-22) to gage the depth of insertion of the distal end portion 312 of the first tubular member 310 relative to the probe 380 when the implant delivery device 302 is moved distally relative to the probe 380. In other embodiments, the proximal end portion of the probe 380 and/or the actuator 370 can include a detent or locking mechanism to ensure that the elongate implant 385 is inserted into the patient's body B at a depth $D_1$ that is substantially the same as the depth $D_P$.

Figure 19:
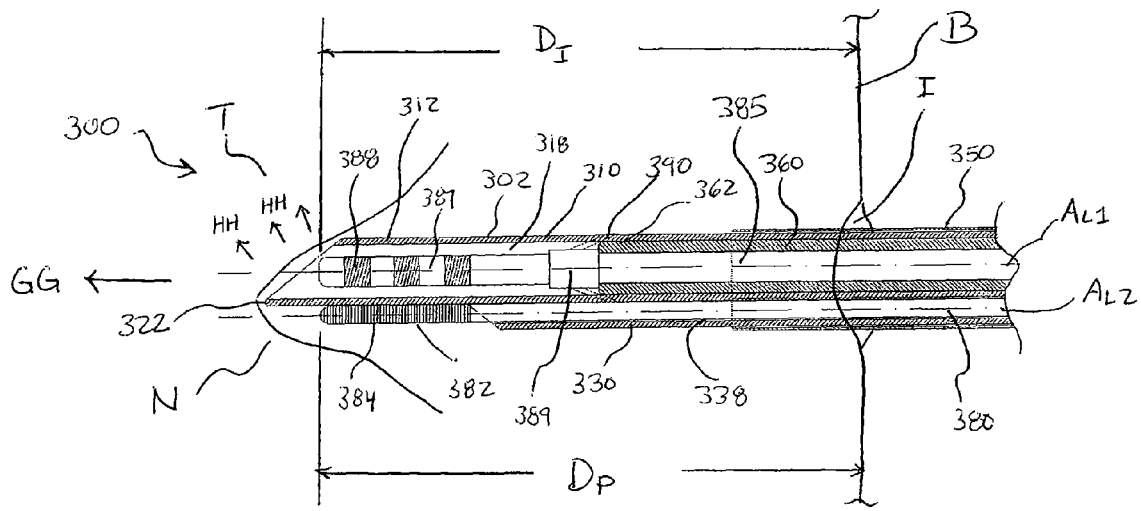
FIG. 19 is a side cross-sectional view of the distal end portion of the medical device shown in FIG. 6 disposed within the patient's body, in a second configuration.

When the implant delivery device 302 is inserted into the patient's body (i.e., when the medical device is moved from its first configuration to its second configuration), the distal end portion 312 of the first tubular member 310 dilates, displaces and/or stretches bodily tissue T as shown by the arrows HH in FIG. 19. As described above, the edge 321 of the first tubular member 310 is devoid of a sharp point such that the distal end portion 312 of the first tubular member 310 can dilate, displace and/or stretch the bodily tissue T without cutting and/or tearing the bodily tissue T. Moreover, the beveled arrangement of the distal end portion 312 of the first tubular member 310 is such that the bodily tissue T can be dilated, displaced and/or stretched in a predetermined direction and/or orientation. Said another way, the beveled arrangement of the distal end portion 312 of the first tubular member 310 is such that the bodily tissue T can be dilated, displaced and/or stretched in a direction away from the target N and/or the distal end portion 382 of the probe 380. In this manner, when the implant delivery device 302 is removed the force exerted by the bodily tissue T as it returns to its initial form urges the elongated implant 385 towards the target N.

Figure 20:
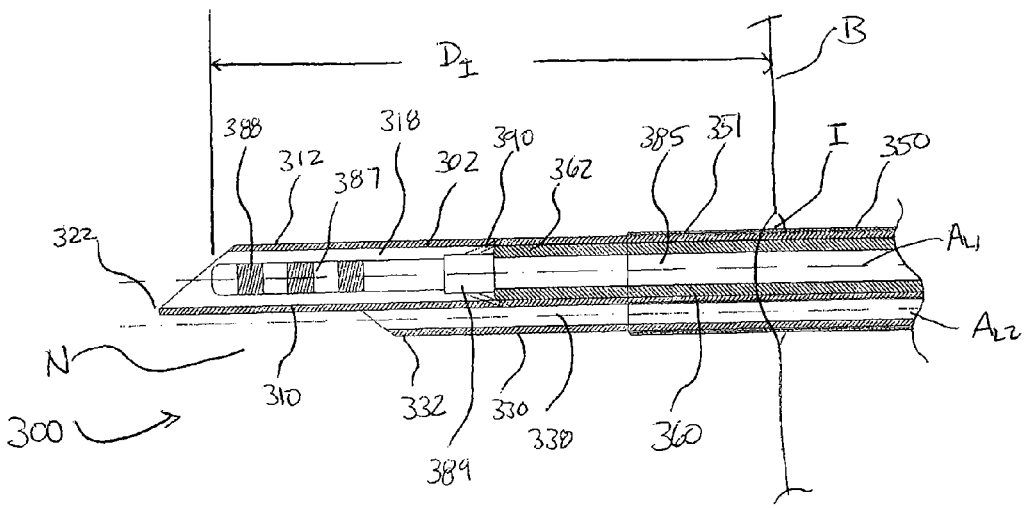
FIG. 20 is a side cross-sectional view of the distal end portion of the medical device shown in FIG. 6 disposed within the patient's body, in a third configuration.

After the distal end portion 312 of the first tubular member 310 is disposed within the patient's body B at the desired depth and/or location, the probe 380 can be removed from the medical device 300, thereby placing the medical device in a third configuration as shown in FIG. 20. More particularly, after the distal end portion 312 of the first tubular member 310 is disposed within the patient's body B at the desired depth and/or location, the probe 380 can be removed from the lumen 318 of the first tubular member 310 in a proximal direction. In other embodiments, the probe 380 can remain in the medical device 300.

Figure 21:
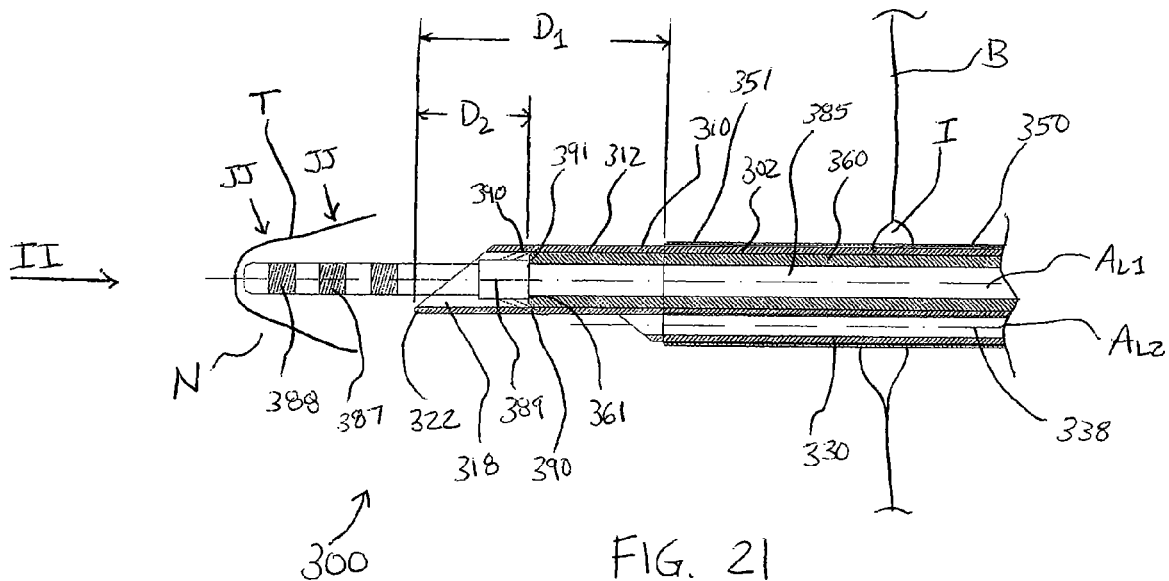
FIG. 21 is a side cross-sectional view of the distal end portion of the medical device shown in FIG. 6 disposed within the patient's body, in a fourth configuration.

After the distal end portion 312 of the first tubular member 310 is disposed within the patient's body B at the desired depth and/or location, the medical device 300 can be placed in a fourth configuration by moving the implant delivery device 302 relative to the sheath 350 and the retainer 360, as shown by the arrow II in FIG. 21. Said another way, the implant delivery device 302 is moved proximally within the sheath 350 until the distal end portion 352 of the sheath 350 is spaced proximally from the distal-most point 322 of the implant delivery device 302 by a distance $D_1$. In this manner, the sheath 350 can be maintained in a constant position within the patient's body B, thereby resulting in accurate placement of the elongate implant within the body. Said yet another way, the implant delivery device 302 is moved proximally about the retainer 360 until the distal end surface 361 of the retainer 360 is spaced proximally from the distal-most point 322 of the implant delivery device 302 by a distance $D_2$.

The medical device 300 can be moved from the third configuration (FIG. 20) to the fourth configuration (FIG. 21) by moving the lever 372 of the actuator 370. In some embodiments, the actuator 370 can include a ratchet mechanism, a detent, or the like to selectively move the implant delivery device 302 relative to the sheath 350 and/or the retainer 360. Said another way, in some embodiments, the actuator 370 can be configured to move the implant delivery device 302 relative to the sheath 350 and/or the retainer 360 in a controlled and/or incremental fashion. Moreover, in some embodiments, the actuator 370 can include a locking mechanism to releasably lock the actuator in a predetermined position.

As shown in FIG. 21, when the medical device 300 is moved from the third configuration to the fourth configuration, the distal end surface 361 of the retainer 360 contacts the shoulder 391 of the anchor portion 389 of the elongate implant 385 such that the elongate implant 385 moves distally within the lumen 318. Accordingly, when the medical device 300 is in the fourth configuration, the electrode array 388 of the elongate implant 385 is disposed outside of the lumen 318 through the opening 324 and adjacent the target N of the patient's body B. As described above, when the implant delivery device 302 moves proximally within the patient's body B, as shown by the arrow II, the bodily tissue T returns to its initial form, as indicated by the arrows JJ. In this manner, the movement of the bodily tissue T exerts a force on the elongate implant 385 thereby urging the elongated implant 385 towards the target N.

When the medical device 300 is in the fourth configuration, the tines 390 of the anchor portion 389 of the elongate implant 385 remain within the lumen 318 of the first tubular member 310. Accordingly, when the medical device is in the fourth configuration, the elongate implant 385 can be moved within the patient's body B by moving the entire medical device 300 to adjust the location and/or orientation of the electrode array 388. In some embodiments, for example, the electrode array 388 can be electrically activated when the medical device 300 is in the fourth configuration to validate the location of the electrode array 388 within the patient's body B.

Figure 22:
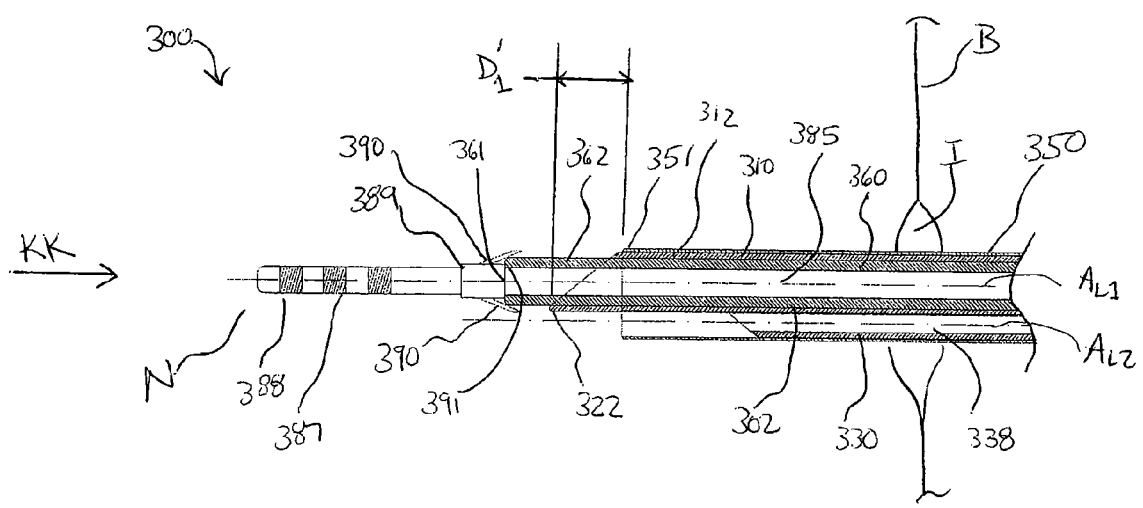
FIG. 22 is a side cross-sectional view of the distal end portion of the medical device shown in FIG. 6 disposed within the patient's body, in a fifth configuration.

A shown in FIG. 22, when the location and/or orientation of the electrode array 388 has been validated, the medical device 300 can be placed in a fifth configuration to complete the insertion of the elongate implant 385 within the patient's body B. The medical device 300 is moved from the fourth configuration to the fifth configuration by moving the implant delivery device 302 relative to the sheath 350 and the retainer 360, as shown by the arrow KK in FIG. 22. Said another way, the implant delivery device 302 is moved proximally within the sheath 350 until the distal end portion 352 of the sheath 350 is spaced proximally from the distal-most point 322 of the implant delivery device 302 by a distance $D'_1$ less than the distance $D_1$. Said yet another way, the implant delivery device 302 is moved proximally about the retainer 360 until the distal end surface 361 of the retainer 360 is spaced distally from the distal-most point 322 of the implant delivery device 302 (i.e., the distal end surface 361 of the retainer 360 is disposed outside of the lumen 318). When the medical device 300 is in the fifth configuration, the tines 390 of the anchor portion 389 of the elongate implant 385 are disposed outside of the lumen 318 of the first tubular member 310. In this manner, the elongate implant 385 can be anchored into the patient's body B in its desired location and/or orientation (e.g., adjacent the target N). After the elongate implant 385 is anchored, the implant delivery device 302 can be removed from the patient's body B via the handle 371 of the actuator 370.

As described above, the medical device 300 can be moved from the fourth configuration (FIG. 21) to the fifth configuration (FIG. 22) by moving the lever 372 of the actuator 370. In some embodiments, for example, the actuator 370 can include a motion-limiter to limit the movement of the implant delivery device 302 within the sheath 350. Similarly, in some embodiments, the actuator 370 can include a locking mechanism to prevent the implant delivery device 302 from "springing back" relative to the sheath 350.

Although the medical device 300 is shown and described above as including one probe 380 and one elongate implant 385, in other embodiments, the medical device 300 can include multiple probes and/or elongate implants. For example, in some embodiments a kit can include an implant delivery device of the types shown and described above. The kit can also include multiple elongate implants of the types shown and described above. In some embodiments, for example, the kit can include multiple elongate implants, each having different characteristics (e.g., size, type of electrode array, polarity, etc.). Similarly, in some embodiments, a kit can include multiple probes of the types shown and described above. In some embodiments, for example, the kit can include multiple probes, each having different characteristics (e.g., length, diameter, type of stimulating electrode, non-electronic, etc.).

The medical devices shown and described herein can be constructed from any suitable material or combination of materials. For example, in some embodiments, an implant delivery device, such as implant delivery device 302, can be a constructed from a rigid material, such as Nylon, a composite material, a metal alloy or the like. In other embodiments, an implant delivery device, such as implant delivery device 302, can be a constructed from a flexible material. In this manner, the implant delivery device can follow a curved passageway within a patient's body.

Figure 23:
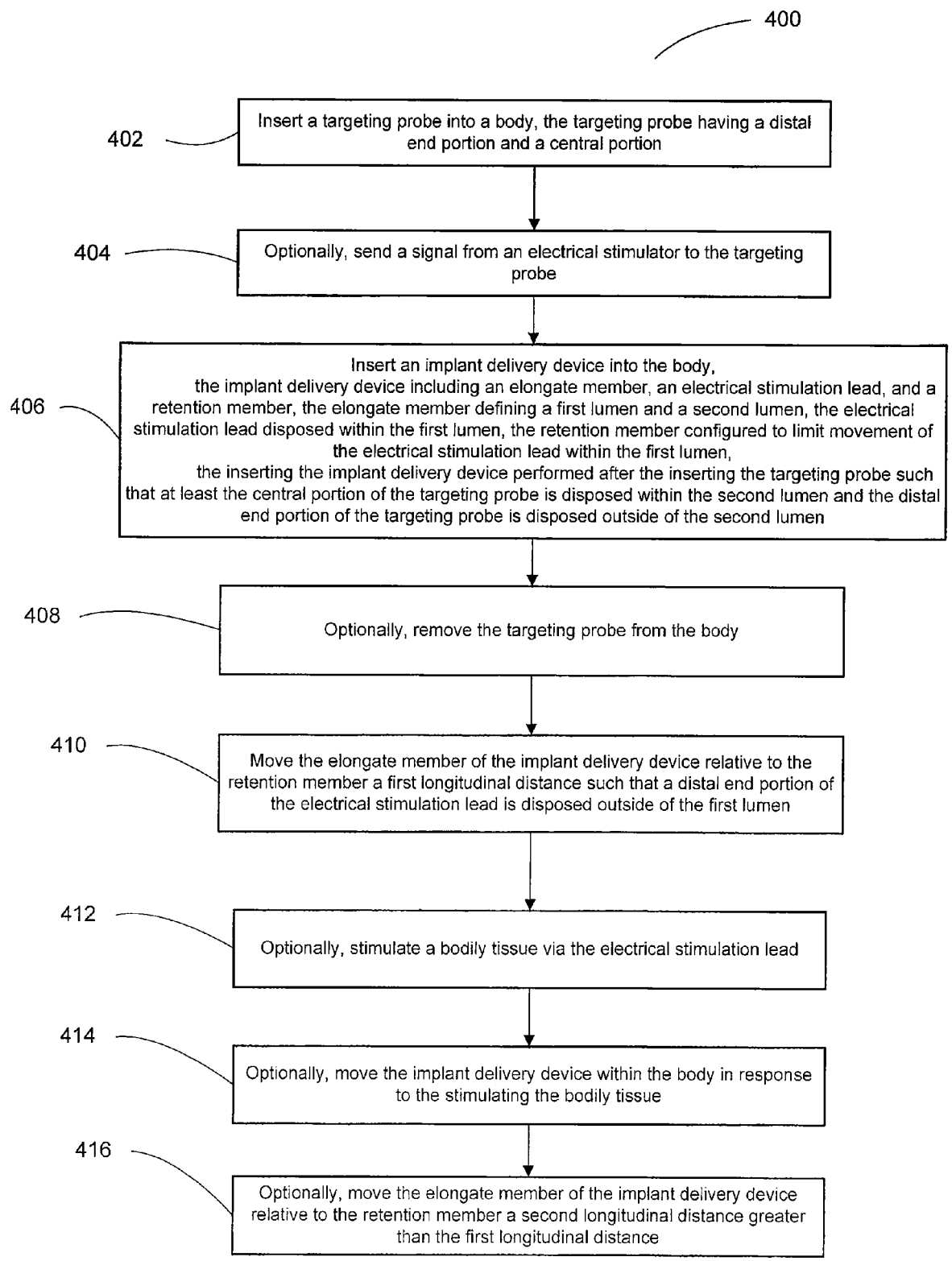
FIG. 23 is a flow chart of a method according to an embodiment of the invention.

FIG. 23 is a flow chart of a method 400 of inserting an elongate implant into a patient's body according to an embodiment of the invention. The method includes inserting a targeting probe into a body, 402. The targeting probe, which can be any targeting probe of the types shown and described above, has a distal end portion and a central portion. For example, in some embodiments, the targeting probe can be a targeting probe 380 shown and described above with reference to FIGS. 6-22. In some embodiments, a signal can be sent from an electrical stimulator to the targeting probe, 404 In this manner, the targeting probe can be used to locate a desired target, such as a nerve or a muscle, within the body.

An implant delivery device is inserted into the body, 406. In some embodiments, the implant delivery device can be inserted percutaneously. The implant delivery device can be any implant delivery device of the types shown and described above, and includes an elongate member, an electrical stimulation lead, and a retention member. The elongate member defines a first lumen and a second lumen. The electrical stimulation lead is disposed within the first lumen. The retention member is configured to limit movement of the electrical stimulation lead within the first lumen. The implant delivery device is inserted after the targeting probe is inserted such that at least the central portion of the targeting probe is disposed within the second lumen and the distal end portion of the targeting probe is disposed outside of the second lumen.

In some embodiments, the implant delivery device is inserted such that a distal end portion of the elongate member dilates, displaces and/or stretches a bodily tissue. For example, in some embodiments, the implant delivery device can include a tapered elongate member configured to dilate the bodily tissue.

In some embodiments, for example, the implant delivery device is inserted such that the distal end portion of the targeting probe is aligned with a distal end portion of the electrical stimulation lead. Similarly, in some embodiments, the implant delivery device is inserted such that an electrode of the electrical stimulation lead is aligned with an electrode of the targeting probe. In some embodiments, the targeting probe can be removed from the body after the implant delivery device is inserted, 408.

The elongate member of the implant delivery device is moved relative to the retention member such that a distal end portion of the electrical stimulation lead is disposed outside of the first lumen, 410. In some embodiments, for example, the elongate member is moved by a first distance such that an anchor portion of the electrical stimulation lead remains disposed within the first lumen. In some embodiments, a target tissue (e.g., a nerve, a muscle or the like) can be stimulated after the elongate member is moved relative to the retention member, 412. In this manner, the location and/or orientation of the electrical stimulation lead within the body can be validated.

In some embodiments, the implant delivery device can optionally be moved within the body in response to the stimulation of the target tissue, 414. In this manner, the location and/or orientation of the electrical stimulation lead can be adjusted in response to the stimulation of the target tissue. Once the location and/or orientation of the electrical stimulation lead has been validated, the method can optionally include moving the elongate member of the implant delivery device relative to the retention member by a second distance greater than the first distance, 416.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above. Thus, the breadth and scope of the invention should not be limited by any of the above-described embodiments. While the invention has been particularly shown and described with reference to specific embodiments thereof, it will be understood that various changes in form and details may be made.

For example, although the distal end portions of the medical devices shown and described above are tapered linearly along a longitudinal axis, in other embodiments, the distal end portion of a medical device can be tapered in a non-linear manner. For example, in some embodiments a medical device can include a first tubular member that is tapered along its longitudinal axis in a curved manner (e.g., a parabolic curve).

Although the medical devices shown and described above are shown as including at least one tubular member defining a lumen having a longitudinal axis that is coaxial with the longitudinal axis of the tubular member, in other embodiments, a medical device can include a tubular member defining a lumen having a longitudinal axis that is non-coaxial with the longitudinal axis of the tubular member. In yet other embodiments, a medical device can include a tubular member defining a lumen having a longitudinal axis that is non-parallel with the longitudinal axis of the tubular member.

Although the medical device 300 is shown and described above as including a first tubular member 310 fixedly coupled to a second tubular member 330, in other embodiments, a medical device can include a first tubular member that is movably coupled to a second tubular member. In this manner, a distance between the distal end surface of the first tubular member and a distal end surface of the second tubular member can be adjustable. In yet other embodiments, a medical device can include a first tubular member that is removably coupled to a second tubular member.

Although the medical devices are shown and described herein as having a distal end portion having an edge devoid of sharp points, in other embodiments, a medical device can have a distal end portion having one or more sharp points configured to cut a bodily tissue.

Although the medical device 300 is shown and described above as include a lever-actuated actuator 370, in other embodiments a medical device can include an automatically actuated actuator. In some embodiments, for example, an actuator can be an electronic actuator that is automatically actuated. Similarly, in some embodiments, a medical device can include an actuator that is biased in a certain position.

Although the medical devices are shown and described above as including an implant delivery device and/or an elongated implant configured to implanted into a patient's body, in some embodiments, a medical device can include a simulated implant delivery device and/or a simulated elongated implant. In such embodiments, for example, the simulated implant delivery device and/or the simulated elongated implant can be configured for use on a simulated target (e.g., a cadaver, a simulated body or the like). In some embodiments, for example, a simulated implant delivery device can correspond to an actual implant delivery device of the types shown and described above and can be used, for example, to train a user in the insertion of elongate implants into a body. Similarly, In some embodiments, for example, a simulated elongate implant can be devoid of an operational electrode array and can be used, for example, to train a user in the insertion of elongate implants into a body.

What is claimed is:

1. An apparatus, comprising:
   a first tubular member defining a longitudinal axis and a lumen substantially coaxial with the longitudinal axis, a distal end portion of the first tubular member being tapered along the longitudinal axis, the lumen of the first tubular member configured to receive at least a portion of an elongate implant;
   a second tubular member defining a longitudinal axis and a lumen substantially coaxial with the longitudinal axis of the second tubular member, the second tubular member coupled to the first tubular member such that the longitudinal axis of the first tubular member is substantially parallel to the longitudinal axis of the second tubular member, a distal end portion of the second tubular member being tapered along the longitudinal axis of the second tubular member;
   a retention member at least partially disposed within the first tubular member, the retention member configured to engage an anchor portion of the elongate implant, the first tubular member configured to move relative to the retention member such that a distal end portion of the retention member and the anchor portion of the elongate implant are within the first tubular member when the first tubular member is in a first position and the distal end portion of the retention member and the anchor portion of the elongate implant are disposed outside of the first tubular member when the first tubular member is in a second position; and
   a sheath slidably disposed about the first tubular member and the second tubular member.

2. The apparatus of claim 1, wherein:
   the distal end portion of the first tubular member is tapered asymmetrically; and
   the distal end portion of the second tubular member is tapered asymmetrically.

3. The apparatus of claim 1, wherein:
   the second tubular member is coupled to a portion of an outer surface of the first tubular member to define an interface portion, the interface portion defining a coupling line substantially parallel to the longitudinal axis of the first tubular member; and
   the distal end portion of the first tubular member is tapered asymmetrically along the longitudinal axis of the first tubular member such that an angle defined by the coupling line and an end surface of the distal end of the first tubular member is greater than ninety degrees.

4. The apparatus of claim 1, wherein:
   the second tubular member is coupled to a portion of an outer surface of the first tubular member to define an interface portion the interface portion defining a coupling line substantially parallel to the longitudinal axis of the first tubular member; and
   the coupling line includes a distal-most point of the distal end portion of the first tubular member.

5. The apparatus of claim 1, wherein:
   a distal-most point of the distal end portion of the first tubular member is disposed at a first position along the longitudinal axis of the first tubular member; and
   a distal-most point of the distal end portion of the second tubular member is disposed at a second position along the longitudinal axis of the second tubular member, the second position being spaced apart proximally from the first position.

6. The apparatus of claim 1, wherein at least a portion of the first tubular member is flexible.

7. The apparatus of claim 1, wherein the first tubular member and the second tubular member are collectively configured to be inserted percutaneously into a body.

8. The apparatus of claim 1, wherein the elongate implant is an electrical stimulation lead.

9. The apparatus of claim 1, wherein:
   the distal end portion of the first tubular member is tapered asymmetrically such that an end surface of the distal end portion of the first tubular member is non-circular.

10. The apparatus of claim 1, wherein a cross-sectional area of the lumen of the first tubular member is different than a cross-sectional area of the lumen of the second tubular member.

11. The apparatus of claim 1, wherein:
    the lumen of the first tubular member has a circular cross-section with a first diameter;
    the lumen of the second tubular member has a circular cross-section with a second diameter; and
    the first diameter being different than the second diameter.

12. The apparatus of claim 1, wherein the first tubular member is rigid.

13. The apparatus of claim 1, further comprising:
    an actuator coupled to at least one of a proximal end portion of the first tubular member and a proximal end portion of the second tubular member, the actuator configured to move the first tubular member and the second tubular member relative to the sheath.

14. The apparatus of claim 1, further comprising:
an electronic probe configured to be movably disposed within the lumen of the second tubular member.

15. The apparatus of claim 1, wherein:
the lumen of the second tubular member is configured to receive at least a portion of an electronic probe; and
the actuator includes an index mechanism to provide an indication of a distance between the distal end portion of the second tubular member and a distal end portion of the electronic probe.

16. An apparatus, comprising:
an implant delivery device configured to deliver an elongate implant into a body, the implant delivery device having a first portion and a second portion, the first portion defining a lumen configured to receive the elongate implant, a distal end portion of the first portion configured to dilate a bodily tissue, the distal end portion of the first portion defining an opening in fluid communication with the lumen,
the second portion defining a lumen configured to receive a targeting probe, a distal end portion of the second portion defining an opening in fluid communication with the lumen of the second portion;
a retention member at least partially disposed within the lumen of the first portion, the retention member configured to selectively retain a portion of the elongate implant; and
a sheath slidably disposed about the implant delivery device,
the implant delivery device configured to move relative to the retention member and the sheath such that a distal end portion of the retention member is within the lumen of the first portion when the implant delivery device is in a first position and the distal end portion of the retention member is disposed outside of the lumen of the first portion when the implant delivery device is in a second position.

17. The apparatus of claim 16, wherein the implant delivery device is rigid.

18. The apparatus of claim 16, wherein a longitudinal axis of the lumen of the first portion is substantially parallel to a longitudinal axis of the lumen of the second portion.

19. The apparatus of claim 16, wherein the distal end portion of the first portion includes an elliptical end surface.

20. The apparatus of claim 16, wherein the distal end portion of the first portion includes a blunt tip configured to dilate the bodily tissue.

21. The apparatus of claim 16, wherein:
an interface of the first portion and the second portion defines a line substantially parallel to a longitudinal axis of the first portion; and
the distal end portion of the first portion is tapered asymmetrically along the longitudinal axis of the first portion such that an angle defined by the line and an end surface of the distal end portion of the first portion is greater than ninety degrees.

22. The apparatus of claim 16, wherein:
the distal end portion of the first portion is disposed at a first position along a longitudinal axis of the first portion; and
the distal end portion of the second portion is disposed at a second position along the longitudinal axis of the first portion, the second position being spaced apart proximally from the first position.

23. The apparatus of claim 16, wherein:
a proximal end portion of the first portion is aligned with a proximal end portion of the second portion;
the first portion has a first length; and
the second portion has a second length less than the first length.

24. The apparatus of claim 16, further comprising:
the elongate implant, the elongate implant including any one of an electrode, an electronic lead or a sensor.

25. The apparatus of claim 16, further comprising:
the targeting probe, the targeting probe including any one of an electronic targeting probe, a radio-opaque targeting probe or a guide wire.

26. The apparatus of claim 16, wherein the implant delivery device is configured to be percutaneously inserted into the body.

27. The apparatus of claim 16, wherein the lumen of the first portion is noncoaxial with the lumen of the second portion.

28. The apparatus of claim 16, wherein the distal end portion of the first portion is tapered along a longitudinal axis of the first portion.

29. The apparatus of claim 16, wherein:
an interface of the first portion and the second portion defines a line substantially parallel to a longitudinal axis of the first portion; and
the line includes a distal-most point of the distal end of the first portion.

30. The apparatus of claim 16, further comprising:
an actuator coupled to a proximal end portion of the implant delivery device and a proximal end portion of the sheath, the actuator configured to move the implant delivery device relative to the sheath.

31. The apparatus of claim 16, further comprising:
an actuator coupled to a proximal end portion of the implant delivery device, the actuator configured to move the implant delivery device relative to the retention member.

32. The apparatus of claim 16, further comprising:
an actuator coupled to a proximal end portion of the implant delivery device, the actuator configured to move the implant delivery device relative to the retention member between the first position and the second position,
the actuator including a locking mechanism to maintain the implant delivery device in the second position.

33. The apparatus of claim 16, further comprising:
an actuator coupled to a proximal end portion of the implant delivery device, the actuator configured to move the implant delivery device relative to the retention member,
the actuator including an index mechanism to provide an indication of a distance between the distal end portion of the second portion of the implant delivery device and a distal end portion of the targeting probe.

34. An apparatus, comprising:
an elongate member configured to insert an electrical stimulation lead into a body, the elongate member having a proximal end portion and a distal end portion, the elongate member defining a first lumen and a second lumen, the distal end portion of the elongate member configured to dilate a bodily tissue, the distal end portion of the elongate member defining a first opening in fluid communication with the first lumen and a second opening in fluid communication with the second lumen;
a retainer slidably disposed within the first lumen;
a sheath slidably disposed about the elongate member; and an actuator coupled to the proximal end portion of the elongate member, the actuator configured to move the elongate member relative to the sheath and the retainer, the actuator including a locking mechanism to limit movement of the elongate member relative to the sheath and the retainer when the elongate member is in a predetermined position relative to the sheath and the retainer.

35. The apparatus of claim 34, wherein the elongate member is rigid.

36. The apparatus of claim 34, wherein a longitudinal axis of the first lumen is substantially parallel to a longitudinal axis of the second lumen.

37. The apparatus of claim 34, wherein the distal end portion of the elongate member is tapered along a longitudinal axis of the elongate member.

38. The apparatus of claim 34, wherein:
the distal end portion of the elongate member includes a first surface defining the first opening and a second surface defining the second opening, the first surface being tapered asymmetrically along a longitudinal axis of the elongate member.

39. The apparatus of claim 34, wherein:
the distal end portion of the elongate member includes a first surface defining the first opening and a second surface defining the second opening, the first surface being angularly offset from a longitudinal axis of the elongate member by an angle greater than zero degrees and less than ninety degrees.

40. The apparatus of claim 34, wherein:
the distal end portion of the elongate member includes a first surface defining the first opening and a second surface defining the second opening;
the first surface of the distal end portion disposed at a first position along a longitudinal axis of the elongate member; and
the second surface of the distal end portion disposed at a second position along the longitudinal axis of the elongate member, the second position being spaced apart proximally from the first position.

41. The apparatus of claim 34, wherein:
the actuator is configured to move the elongate member longitudinally within the sheath when a portion of the sheath and the distal end portion of the elongate member are disposed within the body.

42. The apparatus of claim 34, wherein the actuator includes a detent such that the elongate member can be moved in an incremental manner when the actuator is manipulated.

43. The apparatus of claim 34, wherein:
the retainer is configured to engage an anchor portion of the electrical stimulation lead; and
the elongate member is configured to move relative to the retainer such that a distal end portion of the retainer and the anchor portion of the electrical stimulation lead are within the first lumen when elongate member is in a first position and the distal end portion of the retainer and the anchor portion of the electrical stimulation lead are disposed outside of the first lumen when the elongate member is in a second position.

44. An apparatus, comprising:
a first tubular member defining a longitudinal axis and a lumen substantially coaxial with the longitudinal axis, a distal end portion of the first tubular member being tapered along the longitudinal axis, the lumen of the first tubular member configured to receive at least a portion of an elongate implant;
a second tubular member defining a longitudinal axis and a lumen substantially coaxial with the longitudinal axis of the second tubular member, the second tubular member coupled to the first tubular member such that the longitudinal axis of the first tubular member is substantially parallel to the longitudinal axis of the second tubular member, a distal end portion of the second tubular member being tapered along the longitudinal axis of the second tubular member;
a retention member at least partially disposed within the first tubular member, the retention member configured to engage an anchor portion of the elongate implant, the first tubular member configured to move relative to the retention member such that a distal end portion of the retention member and the anchor portion of the elongate implant are within the first tubular member when the first tubular member is in a first position and the distal end portion of the retention member and the anchor portion of the elongate implant are disposed outside of the first tubular member when the first tubular member is in a second position; and
an actuator coupled to at least one of a proximal end portion of the first tubular member and a proximal end portion of the second tubular member, the actuator configured to move the first tubular member relative to the retention member.

45. The apparatus of claim 44, wherein:
the actuator includes a locking mechanism to maintain the first tubular member in the second position.

46. The apparatus of claim 44, wherein:
the actuator includes a detent such that the first tubular member can be moved in an incremental manner when the actuator is manipulated.

* * * * *